US008835134B2

(12) United States Patent
Han et al.

(10) Patent No.: US 8,835,134 B2
(45) Date of Patent: Sep. 16, 2014

(54) CYCLOASTRAGENOL MONOGLUCOSIDE, PREPARATION, PHARMACEUTICAL COMPOSITION AND APPLICATION THEREOF

(75) Inventors: Yingmei Han, Tianjin (CN); Guangping Xia, Tianjin (CN); Weiren Xu, Tianjin (CN); Zhuanyou Zhao, Tianjin (CN); Wulin Liu, Tianjin (CN); Naxia Zhao, Tianjin (CN); Peng Liu, Tianjin (CN); Shijun Zhang, Tianjin (CN); Xiaoli Fu, Tianjin (CN); Yuli Wang, Tianjin (CN); Weiting Wang, Tianjin (CN); Lida Tang, Tianjin (CN)

(73) Assignee: Tianjin Institute of Pharmaceutical Research, Tianjin (CN)

( * ) Notice: Subject to any disclaimer, the term of this patent is extended or adjusted under 35 U.S.C. 154(b) by 963 days.

(21) Appl. No.: 12/678,025

(22) PCT Filed: Sep. 8, 2008

(86) PCT No.: PCT/CN2008/001594
§ 371 (c)(1),
(2), (4) Date: May 24, 2011

(87) PCT Pub. No.: WO2009/046620
PCT Pub. Date: Apr. 16, 2009

(65) Prior Publication Data
US 2011/0218161 A1    Sep. 8, 2011

(30) Foreign Application Priority Data

Sep. 13, 2007 (CN) .......................... 2007 1 0059591
Jan. 23, 2008 (CN) .......................... 2008 1 0004380

(51) Int. Cl.
*C12P 19/44* (2006.01)
*A61K 36/481* (2006.01)
*A61K 31/7048* (2006.01)
*C12P 19/56* (2006.01)
*C07J 17/00* (2006.01)

(52) U.S. Cl.
CPC ............ *A61K 36/481* (2013.01); *A61K 31/7048* (2013.01); *C12P 19/56* (2013.01); *C07J 17/005* (2013.01)
USPC .......................................................... 435/74

(58) Field of Classification Search
None
See application file for complete search history.

(56) References Cited

U.S. PATENT DOCUMENTS

2006/0292251 A1    12/2006  Lin et al.
2008/0113925 A1     5/2008  Harley et al.

FOREIGN PATENT DOCUMENTS

| CN | 1544458 A | 11/2004 |
| CN | 200310108915 | * 11/2004 |
| CN | 1569884 A | 1/2005 |
| CN | 1669566 A | 9/2005 |
| CN | 1793132 A | 6/2006 |
| CN | 1809364 A | 7/2006 |
| CN | 1854148 A | 11/2006 |
| CN | 1919203 A | 2/2007 |
| WO | WO 98/49153 | * 11/1998 |
| WO | WO-2005/000248 A2 | 1/2005 |

OTHER PUBLICATIONS

Liu et al., A Novel Method for Extraction and Separation of Total Flavones and Total Astragalosides From *Radix astragali*, Chemistry of Natural Compounds, vol. 43, No. 1, 2007.*
Ko et al., Enzymatic Preparation of Ginsenosides Rg2 Rh1, and F1, Chem. Pharm. Bull. 51 (4) 404-408 (2003).*
Kitagawa, et al., "Saponin and Sapogenol. XXXV. 1) Chemical Constituents of Astragali Radix, the Root of *Astragalus membranaceus* Bunge (2). Astragalosides I, II and IV, Acetylastragaloside I and Isoastragalosides I and II". Chem. Pharm. Bull., 1983, vol. 31(2), pp. 698-708.

* cited by examiner

*Primary Examiner* — Bin Shen
(74) *Attorney, Agent, or Firm* — Novak Druce Connolly Bove + Quigg LLP

(57) ABSTRACT

This invention provides a method for preparing cycloastragenol monoglucoside CMG (cycloastragenol-6-O-β-D-glucoside), comprising the steps of: a. using astragaloside IV or Astragali extracts prepared by a conventional method as raw materials and adding an appropriate solvent thereinto to form a raw material solution; b. adding hydrolase and allowing for hydrolysis at a constant temperature to obtain a hydrolysate; c. separating the hydrolysate with macroporous adsorption resin; and d. obtaining the product by purification and separation. The present invention further provides cycloastragenol-6-O-β-D-glucoside prepared according to the method of this invention as well as its use in the preparation of a medicament for treating cardiovascular diseases and pharmaceutical compositions comprising the same.

16 Claims, No Drawings

CYCLOASTRAGENOL MONOGLUCOSIDE, PREPARATION, PHARMACEUTICAL COMPOSITION AND APPLICATION THEREOF

CROSS-REFERENCE TO RELATED APPLICATIONS

This application is a national stage application (under 35 U.S.C. §371) of PCT/CN2008/001594, filed Sep. 8, 2008, which claims benefit of China applications 20070059591.X, filed Sep. 13, 2007 and 200810004380.0, filed Jan. 23, 2008.

TECHNICAL FIELD

The present invention belongs to the field of medical technology. Specifically, this invention relates to a method for preparing cycloastragenol monoglucoside, i.e., cycloastragenol-6-O-β-D-glucoside, and cycloastragenol-6-O-β-D-glucoside prepared by the said method, use of cycloastragenol-6-O-β-D-glucoside in the preparation of a medicament for treating cardiovascular and cerebrovascular diseases and a pharmaceutical composition containing a therapeutically effective amount of cycloastragenol-6-O-β-D-glucoside.

BACKGROUND ART

Cycloastragenol compounds belong to the lanostane tetracyclic triterpenoids in structure, and are indicant ingredient taxa in Astragalus plant. Cycloastragenol triterpenoid saponin ingredients, which are the main bioactive constituents of a common Chinese traditional medicine of Astragali (*Astragalus membranaceus* Bge.), have many pharmacological effects such as immunoregulation, cardiotonic effect, anti-ischemic injury in heart and brain, hepatic protection, anti-inflammation, anti-virus, kidney and pancreatic islet damage improving, and so on. Although the pharmacological effects of astragaloside ingredients has been affirmed, and the industrial production process of the total saponins and monomer saponin (astragaloside IV) are relatively mature (CN1172677C, CN 1543976A, CN 1189176C), this type of compounds are generally with the natures of poor solubility and low bioavailability, which lead to hysteresis of the pharmaceutical research and limit their development and generalization as a medicine, so there is no product on the market as yet.

Cycloastragenol-6-O-β-D-glucoside (CMG) (Formula 1), the structure of which was first reported in 1983 by Isao Kitagawa et al. (Chem. Pharm. Bull. 31 (2) 698-708, 1983), was obtained as a byproduct in hydrolyzing astragaloside IV with hesperidinase to prepare the aglycone thereof in the process of studying the structure of astragaloside IV, however, no report on the pharmacological effects thereof was found in the literature. Our studies reveal that CMG has similar cardiovascular pharmacological activity just as astragaloside IV (see Examples of this application), whereas the solubility thereof is better than that of to astragaloside IV and other known cycloastragenol compounds, so that it is more feasible for CMG to be developed as a medicine. Published invention patent application (international application number: PCT/US2004/020277, Chinese patent application publication number: CN1809364A) describes a method of preparing CMG by hydrolyzing astragaloside IV with a mild acid, wherein the main product actually obtained from the reaction is cycloastragenol (52%) and the yield of CMG is very low (21%); and moreover, due to interference of other byproducts, purification by means of a separation method such as Silica Gel Column Chromatography is needed to get a pure product, which is unsuitable for commercial mass production.

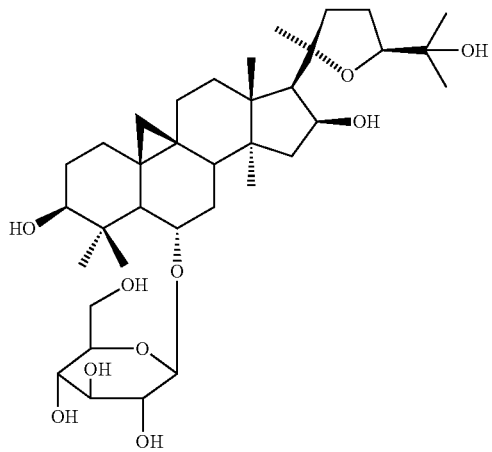

Formula 1

Structure of CMG

DETAILED DESCRIPTION OF THE INVENTION

The inventor addresses technical shortcomings of prior preparation methods by providing a CMG preparation method suitable for industrialized production, and invents relevant formulations on the basis of that CMG has the properties of good solubility and obvious effects of treating cardiovascular diseases.

One of the objects of the present invention is to provide a method for industrially preparing cycloastragenol monoglucoside-cycloastragenol-6-O-β-D-glucoside (CMG). The method prepares CMG with the combination of industrial bionic conversion technology of enzyme preparations and high performance natural product purification technique, without using any noxious organic solvent and strongly acidic or basic reagent. Since the process rute of the instant is method is simple and environmentally friendly and the yield of product of the method is stable, the method is suitable for industrialized production.

Another object of this invention is to provide CMG prepared by the method of the present invention, and pharmaceutical compositions containing a therapeutically effective amount of said CMG and one or more pharmaceutically acceptable adjuvants, and use of said CMG in the preparation of a medicament for treating cardiovascular and cerebrovascular diseases.

The present invention is to be described in detail in combination with the objects of the invention:

The method for preparing CMG of the present invention is achieved through the following technical solutions. Specifically, the present invention provides a method for preparing cycloastragenol-6-O-β-D-glucoside comprising the steps of:

a. using astragaloside IV or Astragali extracts prepared by a conventional method as raw materials and adding an appropriate solvent thereto to form a raw material solution;

b. adding hydrolase and allowing for hydrolysis at a constant temperature to obtain a hydrolysate;

c. separating the hydrolysate with macroporous adsorption resin; and
d. purifying the separated product.

Preferably, when the raw material is astragaloside IV, the concentration of astragaloside IV in the solution is 0.01-1% (W/V), particularly 0.01-0.5% (W/V), more particularly 0.01-0.1% (W/V); and when the raw material is Astragali extracts, the concentration of the solution is such that the ratio of extracts:solution is 1:2-1:1000 (W:V) and preferably, the ratio of extracts:solution is 1:15-1:1000 (W:V). The aforesaid solvent is selected from the group consisting of water, low alcohol, or aqueous low alcohol. Said low alcohol is preferably selected from the group consisting of monohydric alcohols having from 1 to 3 carbon atoms, and more preferably selected from the group consisting of ethanol and methanol, and most preferably being ethanol. When the raw material is astragaloside IV or poorly water soluble extracts, it is necessary to incorporate an appropriate concentration of low alcohol into the raw materials for solubilization, thereby enhancing the efficiency of hydrolysis. The final concentration of low alcohol in the pharmaceutical solution of the invention is preferably in the range of 1-30% (V/V), and more preferably 5-20% (WV).

In a preferred embodiment of the invention, said hydrolase are particularly selected from the group consisting of β-glycosidase, β-glucosidase, hesperidinase or a mixture of one of these enzymes and one or several enzymes selected from the group consisting of cellulase, glucanase, xylanase, glucoamylase, pectinase and amylase, and more preferably selected from the group consisting of β-glycosidase, β-glucosidase or xylanase, and most preferably being xylanase. The xylanase is intended to mean exoxylanase with an enzyme activity of 500-5000 thousands activity units/g (ml).

In another preferred embodiment of the invention, when the substrate is astragaloside IV, the ratio of the substrate to the enzymes is 1:1-50 (W:W); and when the substrate is Astragali extracts, the ratio of the enzymes to the substrate is 1:100-10:1 (W:W), and preferably 1:50-10:1 (W:W).

In yet another preferred embodiment of the invention, the hydrolysis is conducted for 12-72 hours, preferably 48-72 hours, at a constant temperature of 40-55° C., and a suitable pH of the solution is 4-7.

In yet another preferred embodiment of the invention, the above-mentioned separation is conducted via a process comprising the following steps of:
subjecting the hydrolyzate to a macroporous adsorption resin with styrene as the skeleton, and firstly eluting with 1-2 column volumes of water, then eluting with 1-2 column volumes of 0.5-2% alkali solution, and then eluting with 1-3 column volumes of 20-40% ethanol solution, and finally eluting with 1-3 column volumes of 70-95% ethanol, and collecting the portion of eluent eluted with ethanol at a high concentration, followed by vacuum concentration to is a solution which has a small amount of ethanol or is free from alcohol odor so that a white precipitate is visibly produced, wherein when the raw material is the extracts, the ratio of raw material:resin is preferably 1:20-4:1 g:ml, and more preferably 1:10-3:1 g:ml, and when the raw material is astragaloside IV, the ratio of raw material:resin is preferably 0.1:1-20:1 mg:ml, and more preferably 2:1-10:1 mg:ml.

In yet another preferred embodiment of the invention, the above-mentioned purification is conducted via a process comprising the following steps of:
filtering the white precipitate obtained by separation, re-dissolving it in a low alcohol, filtering and concentrating the filtrate until slight turbidity is observed, and then being kept for crystallization; filtering to obtain the crystal, and then recrystallizing it with a low alcohol or an aqueous low alcohol so that cycloastragenol-6-O-β-D-glucoside with a purity of more than 95% is obtained. The low alcohol used herein is preferably chosen from monohydric alcohols having from 1 to 5 carbon atoms or polyhydric alcohols, and more preferably chosen from methanol and ethanol.

The present invention further provides cycloastragenol-6-O-β-D-glucoside prepared by the method of this invention. The cycloastragenol-6-O-β-D-glucoside of the present invention is in the form of a white fine acicular crystal (methanol or ethanol-water) or an amorphous powder (other solvents).

The present invention further provides a pharmaceutical composition comprising a therapeutically effective amount of cycloastragenol-6-O-β-D-glucoside prepared by the method of this invention and a pharmaceutically acceptable adjuvant.

Preferably, the above-mentioned pharmaceutically acceptable adjuvant is selected from the group consisting of diluents, lubricants, adhesives, disintegrants, stabilizers and solvents. Said diluents include, but not limited to, starch, microcrystalline cellulose, sucrose, dextrin, lactose, powdered sugar, glucose, low molecular weight dextran, kaolin, sodium chloride, mannitol, etc. Said lubricants include, but not limited to, magnesium stearate, stearic acid, boric acid, sodium chloride, sodium oleate, DL-leucine, lauryl sodium sulfate, polyethylene glycol 4000-6000, poloxamer, etc. Said adhesives include, but not limited to, water, ethanol, starch slurry, syrup, gelatin, methyl cellulose, hydroxypropyl methyl cellulose, carboxymethyl sodium cellulose, sodium alginate, Ghatti gum, polyvinylpyrrolidone, etc. Said disintegrants include, but not limited to, starch, carboxymethyl starch sodium, effervescent mixture (i.e., sodium bicarbonate and citric acid, tartaric acid, low substituted hydroxypropyl cellulose), etc. Said stabilizers include, but not limited to, polysaccharides such as arabic gum, agar, alginic acid, guar gum, gum tragacanth, acrylic ester resin, cellulose ethers and carboxymethyl chitin, etc. Said solvents include, but not limited to, Ringer's solution, water, phosphate buffer, balanced salt solution, etc.

The combining proportion of the active ingredients and auxiliary ingredients varies depending on different formulations, and the dosage of the active ingredients may be 0.01 mg/kg to 50 mg/kg which may vary depending on different purposes of therapy.

The pharmaceutical composition of this invention may be in the form of solid oral formulations, liquid oral formulations, injections, films or aerosols. The aforesaid solid oral formulations are preferably common tablets, dispersible tablets, enteric tablets, granules, capsules, dripping pills or pulvis, or sustained- or controlled-release formulations. Said sustained- or controlled-release formulations are preferably sustained- or controlled-release tablets, granules, or capsules. The aforesaid liquid oral formulations are preferably oral solutions or emulsions. The aforesaid injections are preferably vial injections, infusion solutions or freeze-dried powders for injection.

When the pharmaceutical composition of the present invention is in the form of vial injection, the composition may preferably further contain, besides water for injection, a proper proportion of a pharmaceutical adjuvant selected from the group consisting of glucose, sodium chloride, sorbitol and phosphate, an organic solvent selected from the group consisting of ethanol, glycerin and propanediol, or a cosolvent selected from the group consisting of PEGs for injection and hydroxypropyl-β-cyclodextrin. When the pharmaceutical composition of the present invention is in the form of infusion solution, the composition may preferably further contain, besides water for injection, glucose, sodium chloride and/or an isosmotic agent, which is added as necessary. When the pharmaceutical composition of the present invention is in the form of freeze-dried powder for injection, the composition may preferably further contain a proper proportion of freeze-drying support agent that is preferably selected from the group consisting of one, two, or a combination of more than two of mannitol, glucose, sorbitol, sodium chloride, dextran, sucrose, lactose, hydrolyzed gelatin, hydroxypropyl-β-cyclodextrin, sulfobutyl ether cyclodextrin, poloxamer and polyethylene glycol.

In the pharmaceutical composition of the present invention, the weight ratio of cycloastragenol-6-O-β-D-glucoside to the pharmaceutically acceptable adjuvants in the above-mentioned freeze-dried powder for injection is preferably in the range of 1:10-200, more preferably 1:50-200, and still more preferably 1:100-150.

Preferably, the aforesaid freeze-drying support agent is mannitol or mannitol-lactose composition. The weight ratio of mannitol to lactose in the mannitol-lactose composition is in the range of 10:1-1:1, and preferably in the range of 5:1-1:1.

The aforesaid freeze-drying support agent is dextran, polyethylene glycol-mannitol composition or dextran-polyethylene glycol-mannitol composition, and polyethylene glycol-mannitol composition is preferred. The polyethylene glycol is preferably polyethylene glycol 200-600, and more preferably polyethylene glycol 400. As for the polyethylene glycol-mannitol composition, the weight ratio of polyethylene glycol:mannitol is 1:1-1:10, and preferably 1:1-1:5.

The present invention further provides the use of cycloastragenol-6-O-β-D-glucoside prepared by the method of this invention in the preparation of a medicament for treating cardiovascular and cerebrovascular diseases.

In the technical solution of preparing CMG provided by the invention, the concentration of the substrate solution and the mixing ratio of enzyme to the substrate are the main factors affecting the yield of CMG. When the concentration of the substrate solution is too high, the efficiency of hydrolysis would be lowered due to influence on the activity of enzyme; and when the substrate solution is too dilute, the volume of the solution and the consumption of enzyme would be unnecessarily enhanced and the processing time would be prolonged, consequently affecting the production cycle. Generally, when the substrate is crude extracts of Astragali (the content of astragaloside IV is 0.2-8%), the dilution factor of the substrate solution can be somewhat low (the ratio of extracts: solution is 1:5-1:30 W:V); when the substrate is refined extracts (the content of astragaloside IV is 1-50%), the dilution factor of the substrate solution (extracts-solution ratio) should be 1:40-1:1000 W:V; and when the content of astragaloside IV in the substrate is higher than 50%, the substrate solution should be formulated according to the formulation procedures for astragaloside IV solution.

The method for preparing CMG compound provided by the invention may also be carried out by preparing CMG directly from herbal Astragali, without the need of firstly preparing a high purity of astragaloside IV and then preparing the desired compound therefrom. Therefore, the method for preparing CMG compound provided by the invention significantly saves production costs, and the process route thereof is simple. Since bio-enzymatic hydrolysis process is adopted, there is no need of use of any noxious organic solvent throughout the technological process, which makes the feasibility of practical production high and renders the yield of product (average 0.1% from herbs) and the quality of product stable.

The CMG compound provided by the invention has a higher water solubility than is that of other cycloastragenol ingredients, and is suitable for being formulated into injection preparations. Injection preparations possess certain advantages in clinical practice due to their fast and stable treatment effects and suitability for critical patients or patients unable to take medicine orally.

When the CMG compound is formulated into a vial injection, it can be prepared according to a conventional preparation method for vial injection by directly dissolving the CMG compound in water for injection and adding an appropriate proportion of glucose, sodium chloride, sorbitol, phosphate and the like. However, the addition of organic solvents such as ethanol, glycerol, propanediol, or cosolvents such as PEGs for injection, hydroxypropyl-β-cyclodextrin, is required for preparing large-dose injections with high concentration.

When the pharmaceutical composition of the invention is a vial injection, the concentration of cycloastragenol-6-O-β-D-glucoside in the vial injection is preferably 0.01%-1% g/100 ml, and more preferably 0.01%-0.2% g/100 ml.

When the CMG compound is formulated into an infusion solution, various specifications of infusion solutions can be prepared according to a conventional preparation method for infusion solution by dissolving a prescribed amount of the CMG compound in water for injection and adding, as necessary, glucose, sodium chloride and an isosmotic agent.

When the pharmaceutical composition of the invention is an infusion solution, the concentration of cycloastragenol-6-O-β-D-glucoside in the infusion solution is preferably 0.001%-0.1% g/100 ml, and more preferably 0.002%-0.05% g/100 ml.

When the CMG compound is formulated into a freeze-dried powder for injection, to a proper proportion of freeze-drying support agent may be added as required for formulations. Said support agent is selected from the group consisting of one, two, or a combination of more than two of mannitol, glucose, sorbitol, sodium chloride, dextran, sucrose, lactose, hydrolyzed gelatin, hydroxypropyl-β-cyclodextrin, sulfobutyl ether cyclodextrin, poloxamer and is polyethylene glycol.

An appropriate proportion of freeze-drying support agent can increase the solubility of the compound and make the products have better appearance and stability. Therefore, the proportion of the freeze-drying support agent and the selection of suitable freeze-drying support agents play a very important role to the quality of the final product. In the CMG freeze-dried powder of the invention, the weight ratio of CMG to pharmaceutically acceptable adjuvants is 1:10-200, and preferably 1:50-200, and more preferably 1:100-150.

The freeze-drying support agent of the invention is further preferably mannitol or mannitol-lactose composition, and the weight ratio of mannitol to lactose in the mannitol-lactose composition may be 10:1-1:1 (W:W), and preferably 5:1-1:1

Further more preferably, the freeze-drying support agent of the invention is dextran, polyethylene glycol-mannitol or dextran-polyethylene glycol-mannitol composition, wherein polyethylene glycol-mannitol composition is most preferred. Said polyethylene glycol is preferably polyethylene glycol 200-600, and more preferably polyethylene glycol 400. As for polyethylene glycol-mannitol composition, the weight ratio of polyethylene glycol:mannitol is 1:1-1:10, preferably 1:1-1:5, and more preferably 1:1-1:2.

The CMG freeze-dried powder provided by the invention may be prepared through conventional preparation processes in the art. However, the solubility of CMG in water is limited, and it is significantly affected under different dissolution conditions. Therefore, in order to ensure the uniformity of the pharmaceutical content in every batch of product and meet the requirements for the concentration of solution of the freeze-dried powder, it is necessary to take appropriate measures in the manufacturing process, especially in the process of solution preparation.

The above-mentioned problems were solved through the following steps in this invention:
a. dissolving a prescribed amount of sample in a solvent that is treated with 0.1-0.5% of activated carbon;
b. adding dropwise the sample solution of step a while stirring into a solution of a freeze-drying support agent that is treated with 0.1-0.5% of activated carbon; and
c. adding water to the prescribed volume, membrane filtering, subpackaging, and freeze-drying.

In the above preparation steps of said freeze-dried powder, the solvent of step a is preferably ethanol, propanediol or polyethylene glycol, and its amount is preferably 1-10% of the total volume of the prescribed amount of the solution.

BEST MODE FOR CARRYING OUT THE INVENTION

Hereinafter, the present invention will be explained in more detail with reference to the following examples which are presented for the purposes of delivering a more comprehensive understanding of the present invention to those skilled in the art and are not to be construed as limiting the scope of the invention.

Example 1

150 ml medicinal ethanol was added to 2 g astragaloside IV to dissolve it while heating, and then water was added to dilute the resulting solution to 3000 ml, followed by the addition and dissolution of 30 g β-glycosidase. Then the pH of the solution was adjusted to 5.0. The mixture was allowed to undergo enzymatic hydrolysis for 24 hours at a constant temperature of 45° C., and then filtered. The filtrate was subjected to adsorption using a 500 ml macroporous adsorption resin D101, and eluted successively with 2 column volumes of water, 0.5% sodium hydroxide solution and 30% ethanol solution respectively, and finally eluted with 2 column volumes of 70% ethanol, and the resulting eluent of 70% ethanol was collected, followed by vacuum concentration till no odour of alcohol can be detected, and a white precipitate was observed to settle out. The precipitate was obtained via filtration, and re-dissolved with 95% ethanol, then filtered, and the is filtrate was concentrated till the solution began to become turbid, and then kept for crystallization. The crystal, i.e., a purified CMG (white fine acicular powder), was obtained after filtration.

Example 2

540 g water decoction extracts of herb Astragali (2 kg) was diluted with water to the extent that the ratio of extracts:medicinal solution is 1:15 W:V, then 90 g β-glucosidase was added and dissolved thereinto, and then the pH of the solution was adjusted to 6.0. The mixture was allowed to undergo enzymatic hydrolysis for 48 hours at 40° C., and then filtered. The filtrate was subjected to adsorption using a 500 ml macroporous adsorption resin AB-8, and eluted successively with 1 column volume of water, 2 column volumes of 0.5% sodium hydroxide solution and 2 column volumes of 40% ethanol solution, and finally eluted with 2 column volumes of 80% ethanol, and the resulting eluent of 80% ethanol was collected, followed by vacuum concentration till no odour of alcohol can be detected. The resultant was placed till a white precipitate was settled out. The white precipitate was obtained via filtration, re-dissolved with 95% ethanol, and then filtered, and the filtrate was concentrated till the solution began to become turbid, and then kept for crystallization. A purified CMG (white amorphous powder) was obtained after filtration.

Example 3

300 g alcohol extracts of herb Astragali was diluted with water to the extent that the ratio of extracts:medicinal solution is 1:20 W:V, then 50 g glucanase and 50 g β-glucosidase were added and dissolved thereinto, and then the pH of the solution was adjusted to 5.5. The mixture was allowed to undergo enzymatic hydrolysis for 24 hours at 50° C., and then filtered. The filtrate was subjected to adsorption using a 400 ml macroporous adsorption resin D101, and eluted successively with 2 column volumes of water, 2 column volumes of 1% sodium hydroxide solution and 2 column volumes of 40% ethanol solution, and finally eluted with 2 column volumes of 80% ethanol, and the resulting eluent of 80% ethanol was collected, followed by vacuum concentration till no odour of alcohol can be detected. The resultant was placed till a white precipitate was settled out. The white precipitate was obtained via filtration, re-dissolved with methanol, and then filtered, and the filtrate was concentrated till the solution began to become turbid, and then kept for crystallization. The crystal was obtained after filtration and then recrystallized from ethanol-water, and a purified CMG (white amorphous powder) was obtained.

Example 4

4000 ml water was added to 2 g astragaloside IV to form a suspension, and 40 g β-glucosidase was added and dissolved thereinto, and then the pH of the solution was adjusted to 6.5. The mixture was allowed to undergo enzymatic hydrolysis for 48 hours at 45° C., and then filtered. The filtrate was subjected to adsorption using a 400 ml macroporous adsorption resin D101, and eluted successively with 2 column volumes of water and 40% ethanol solution respectively, and finally eluted with 2 column volumes of 70% ethanol, and the resulting eluent of 70% ethanol was collected, followed by vacuum concentration till no odour of alcohol can be detected. The resultant was placed till a white precipitate was settled out. The white precipitate was obtained via filtration, re-dissolved with methanol, and then filtered, and the filtrate was concentrated till the solution began to become turbid, and then kept for crystallization. The crystal was obtained after filtration and then recrystallized from methanol-water, and a purified CMG (white fine acicular crystal) was obtained.

Example 5

Water decoction extracts (with an extract rate of 32%) of herb Astragali (2 kg) was concentrated till the ratio of extracts:solution is 1:10 W:V, then 80 g β-glucosidase was added and dissolved thereinto, and then the pH of the solution was adjusted to 6.5. The mixture was allowed to undergo enzymatic hydrolysis for 24 hours at 45° C., and then filtered. The filtrate was subjected to adsorption using a 600 ml macroporous adsorption resin D101, and eluted successively with 1 column volume of water, 2 column volumes of 0.5% sodium hydroxide solution and 2 column volumes of 40% ethanol solution, and finally eluted with 2 column volumes of 70% ethanol, and the resulting eluent of 70% ethanol was collected, followed by vacuum concentration till no odour of alcohol can be detected. The is resultant was placed till a white precipitate was settled out. The white precipitate was obtained via filtration, re-dissolved with ethanol, and then filtered, and the filtrate was concentrated till the solution began to become turbid, and then kept for crystallization. The crystal was obtained after filtration and then recrystallized from ethanol-water, and a purified CMG (white amorphous powder) was obtained.

Example 6

Water decoction-alcohol precipitation extracts (with an extract rate of 23%) of herb Astragali (2 kg) was diluted with water to the extent that the ratio of extracts:medicinal solution is 1:30 W:V, then 50 g cellulase, 50 g glucanase and 130 g β-glucosidase were added and dissolved thereinto, and then the pH of the solution was adjusted to 4.5. The mixture was allowed to undergo enzymatic hydrolysis for 72 hours at 45° C., and then filtered. The filtrate was subjected to adsorption using a 400 ml macroporous adsorption resin D101, and eluted successively with 1 column volume of water, 2 column volumes of 0.5% sodium hydroxide solution and 2 column volumes of 40% ethanol solution, and finally eluted with 2 column volumes of 70% ethanol, and the resulting eluent of 70% ethanol was collected, followed by vacuum concentration till no odour of alcohol can be detected. The resultant was placed till a white precipitate was settled out. The white precipitate was obtained via filtration, re-dissolved with ethanol, and then filtered, and the filtrate was concentrated till the solution began to become turbid, and then kept for crystallization. The crystal was obtained after filtration and recrystallized from ethanol-water, and then a purified CMG (white amorphous powder) was obtained.

Example 7

Water decoction extracts (with an extract rate of 29%) of herb Astragali (2 kg) was concentrated till the ratio of extracts:medicinal solution is 1:25 W:V, then 50 g cellulase, 15 g pectinase and 80 g β-glucosidase were added and dissolved thereinto, and then the pH of the solution was adjusted to 5.0. The mixture was allowed to undergo enzymatic hydrolysis for 24 hours at 40° C., and then filtered. The filtrate was subjected to adsorption using a 500 ml macroporous adsorption resin D101, and eluted successively with 2 column volumes of water, 2 column volumes of 0.5% sodium hydroxide solution and 2 column volumes of 40% ethanol solution, and finally eluted with 2 column volumes of 70% ethanol, and the resulting eluent of 70% ethanol was collected, followed by vacuum concentration till no odour of alcohol can be detected. The resultant was placed till a white precipitate was settled out. The subsequent procedures are the same as those of Example 6.

Example 8

300 ml ethanol was added to 2 g astragaloside IV to dissolve it, and water was added to dilute the resulting solution to 1000 ml, and then 10 g β-glucosidase were added and dissolved thereinto, and then the pH of the solution was adjusted to 5.5. The mixture was allowed to undergo enzymatic hydrolysis for 72 hours at 45° C., and then filtered. The filtrate was subjected to adsorption using a 200 ml macroporous adsorption resin D101, and eluted successively with 1 column volume of water, 2 column volumes of 0.5% sodium hydroxide solution and 2 column volumes of 40% ethanol solution, and finally eluted with 2 column volumes of 70% ethanol, and the resulting eluent of 70% ethanol was collected, followed by vacuum concentration till no odour of alcohol can be detected. The subsequent procedures are the same as those of Example 6.

Example 9

30 g extracts of herb Astragali was formulated with water to the extent that the ratio of extracts:medicinal solution is 1:30 W:V, then 30 g β-glucosidase was added and dissolved thereinto, and then the pH of the solution was adjusted to 6.0. The mixture was allowed to undergo enzymatic hydrolysis for 48 hours at 45° C., and then filtered. The filtrate was subjected to adsorption using a 700 ml macroporous adsorption resin D101, and eluted successively with 1 column to volume of water, 2 column volumes of 0.5% sodium hydroxide solution and 2 column volumes of 40% ethanol solution, and finally eluted with 2 column volumes of 70% ethanol, and the resulting eluent of 70% ethanol was collected, followed by vacuum concentration till no odour of alcohol can be detected. The subsequent procedures are the same as those of Example 6.

Example 10

20 g extracts of herb Astragali was dissolved in water, and diluted with water to the extent that the ratio of extracts:medicinal solution is 1:40 W:V, then 2 g β-glucosidase and 3 g xylanase were added and dissolved thereinto, and then the pH of the solution was adjusted to 5.0. The mixture was allowed to undergo enzymatic hydrolysis for 48 hours at 40° C., and then filtered. The filtrate was subjected to adsorption using a 600 ml macroporous adsorption resin D101, and eluted successively with 1 column volume of water, 2 column volumes of 0.5% sodium hydroxide solution and 2 column volumes of 40% ethanol solution, and finally eluted with 2 column volumes of 70% ethanol, and the resulting eluent of 70% ethanol was collected, followed by vacuum concentration till no odour of alcohol can be detected. The subsequent procedures are the same as those of Example 6.

Example 11

Water decoction extracts (with an extract rate of 32%) of herb Astragali (2 kg) was concentrated till the ratio of extracts:medicinal solution is 1:7 W:V, then 40 g β-glucosidase, 10 g glucoamylase and 14 g xylanase were added and dissolved thereinto, and then the pH of the solution was adjusted to 7.0. The mixture was allowed to undergo enzymatic hydrolysis for 72 hours at 40° C., and then filtered. The filtrate was subjected to adsorption using a 800 ml macroporous adsorption resin D101, and eluted successively with 1 column volume of water, 2 column volumes of 0.5% sodium hydroxide solution and 2 column volumes of 40% ethanol solution, and finally eluted with 2 column volumes of 70% ethanol, and the resulting eluent of 70% ethanol was collected, followed by vacuum concentration till no odour of alcohol can be detected. The subsequent procedures are the same as those of Example 6.

Example 12

Water decoction extracts (with an extract rate of 32%) of herb Astragali (2 kg) was concentrated till the ratio of extracts:medicinal solution is 1:12 W:V, then 32 g β-glucosidase was added and dissolved thereinto, and then the pH of the solution was adjusted to 5.5. The mixture was allowed to undergo enzymatic hydrolysis for 72 hours at 40° C., and then filtered. The filtrate was subjected to adsorption using a 500 ml macroporous adsorption resin D101, and eluted successively with 1 column volume of water, 2 column volumes of 0.5% sodium hydroxide solution and 2 column volumes of 40% ethanol solution, and finally eluted with 2 column volumes of 70% ethanol, and the resulting eluent of 70% ethanol was collected, followed by vacuum concentration till no odour of alcohol can be detected. The subsequent procedures are the same as those of Example 6.

Example 13

15 g extracts of herb Astragali was dissolved in water, and diluted with water to the extent that the ratio of extracts:medicinal solution is 1:60 W:V, then 1 g β-glucosidase was added and dissolved thereinto, and then the pH of the solution was adjusted to 4.5. The mixture was allowed to undergo enzymatic hydrolysis for 48 hours at 50° C., and then filtered. The filtrate was subjected to adsorption using a 400 ml macroporous adsorption resin D101, and eluted successively with 1 column volume of water, 2 column volumes of 0.5% sodium hydroxide solution and 2 column volumes of 40% ethanol solution, and finally eluted with 2 column volumes of 70% ethanol, and the resulting eluent of 70% ethanol was collected, followed by vacuum concentration till no odour of alcohol can be detected. The subsequent procedures are the same as those of Example 6.

Example 14

30 g extracts of herb Astragali was dissolved in water, and diluted with water to the extent that the ratio of extracts:medicinal solution is 1:80 W:V, then 3 g β-glycosidase was added and dissolved thereinto, and then the pH of the solution was adjusted to 5.0. The mixture was allowed to undergo enzymatic hydrolysis for 48 hours at 50° C., and then filtered. The filtrate was subjected to adsorption using a 250 ml macroporous adsorption resin D101, and eluted successively with 1 column volume of water, 2 column volumes of 0.5% sodium hydroxide solution and 2 column volumes of 40% ethanol solution, and finally eluted with 2 column volumes of 70% ethanol, and the resulting eluent of 70% ethanol was collected, followed by vacuum concentration till no odour of alcohol can be detected. The subsequent procedures are the same as those of Example 6.

Example 15

Ethanol extracts (with an extract rate of 24%) of herb Astragali (2 kg) was dissolved in water, and diluted with water to the extent that the ratio of extracts:medicinal solution is 1:20 W:V, then 96 g β-glucosidase was added and dissolved thereinto, and then the pH of the solution was adjusted to 6.0. The mixture was allowed to undergo enzymatic hydrolysis for 24 hours at 45° C., and then filtered. The filtrate was subjected to adsorption using a 200 ml macroporous adsorption resin D101, and eluted successively with 1 column volume of water, 2 column volumes of 0.5% sodium hydroxide solution and 2 column volumes of 40% ethanol solution, and finally eluted with 2 column volumes of 70% ethanol, and the resulting eluent of 70% ethanol was collected, followed by vacuum concentration till no odour of alcohol can be detected. The subsequent procedures are the same as those of Example 6.

Example 16

200 g extracts of herb Astragali was dissolved in water, and diluted with water to the extent that the ratio of extracts:medicinal solution is 1:90 W:V, then 5 g β-glucosidase and 5 g amylase were added and dissolved thereinto, and then the pH of the solution was adjusted to 5.5. The mixture was allowed to undergo enzymatic hydrolysis for 12 hours at 40° C., and then filtered. The filtrate was subjected to adsorption using a 300 ml macroporous adsorption resin D101, and eluted successively with 1 column volume of water, 2 column volumes of 0.5% sodium hydroxide solution and 2 column volumes of 40% ethanol solution, and finally eluted with 2 column volumes of 70% ethanol, and the resulting eluent of 70% ethanol was collected, followed by vacuum concentration till no odour of alcohol can be detected. The subsequent procedures are the same as those of to Example 6.

Example 17

Ethanol extracts (with an extract rate of 20%) of herb Astragali (2 kg) was dissolved in water, and diluted with water to the extent that the ratio of extracts:medicinal solution is 1:100 W:V, then 10 g β-glucosidase was added and dissolved thereinto, and then the pH of the solution was adjusted to 6.0. The mixture was allowed to undergo enzymatic hydrolysis for 48 hours at 45° C., and then filtered. The filtrate was subjected to adsorption using a 1000 ml macroporous adsorption resin D101, and eluted successively with 1 column volume of water, 2 column volumes of 0.5% sodium hydroxide solution and 2 column volumes of 40% ethanol solution, and finally eluted with 2 column volumes of 70% ethanol, and the resulting eluent of 70% ethanol was collected, followed by vacuum concentration till no odour of alcohol can be detected. The subsequent procedures are the same as those of Example 6.

Example 18

200 g extracts of herb Astragali was dissolved in water, and diluted with water to the extent that the ratio of extracts:medicinal solution is 1:10 W:V, then 4 g β-glucosidase was added and dissolved thereinto, and then the pH of the solution was adjusted to 6.0. The mixture was allowed to undergo enzymatic hydrolysis for 36 hours at 50° C., and then filtered. The filtrate was subjected to adsorption using a 500 ml macroporous adsorption resin D101, and eluted successively with 1 column volume of water, 2 column volumes of 0.5% sodium hydroxide solution and 2 column volumes of 40% ethanol solution, and finally eluted with 2 column volumes of 70% ethanol, and the resulting eluent of 70% ethanol was collected, followed by vacuum concentration till no odour of alcohol can be detected. The subsequent procedures are the same as those of Example 6.

Example 19

30 g extracts of herb Astragali was dissolved in water, and diluted with water to the extent that the ratio of extracts:medicinal solution is 1:20 W:V, then 1 g β-glucosidase was added and dissolved thereinto, and then the pH of the solution was adjusted to 5.0. The mixture was allowed to undergo enzymatic hydrolysis for 24 hours at 40° C., and then filtered.

The filtrate was subjected to adsorption using a 50 ml macroporous adsorption resin D101, and eluted successively with 1 column volume of water, 2 column volumes of 0.5% sodium hydroxide solution and 2 column volumes of 40% ethanol solution, and finally eluted with 2 column volumes of 70% ethanol, and the resulting eluent of 70% ethanol was collected, followed by vacuum concentration till no odour of alcohol can be detected. The subsequent procedures are the same as those of Example 6.

Example 20

5 g extracts of herb Astragali was dissolved in water, and diluted with water to the extent that the ratio of extracts: medicinal solution is 1:100 W:V, then 50 g β-glucosidase was added and dissolved thereinto, and then the pH of the solution was adjusted to 5.5. The mixture was allowed to undergo enzymatic hydrolysis for 24 hours at 45° C., and then filtered. The filtrate was subjected to adsorption using a 100 ml macroporous adsorption resin D101, and eluted successively with 1 column volume of water, 2 column volumes of 0.5% sodium hydroxide solution and 2 column volumes of 40% ethanol solution, and finally eluted with 2 column volumes of 70% ethanol, and the resulting eluent of 70% ethanol was collected, followed by vacuum concentration till no odour of alcohol can be detected. The subsequent procedures are the same as those of Example 6.

Example 21

1 g extracts of herb Astragali was dissolved in water, and diluted with water to the extent that the ratio of extracts: medicinal solution is 1:80 W:V, then 5 g β-glucosidase was added and dissolved thereinto, and then the pH of the solution was adjusted to 5.5. The mixture was allowed to undergo enzymatic hydrolysis for 72 hours at 45° C., and then filtered. The filtrate was subjected to adsorption using a 20 ml macroporous adsorption resin D101, and eluted successively with 1 column volume of water, 2 column volumes of 0.5% sodium hydroxide solution and 2 column volumes of 40% ethanol solution, and finally eluted with 2 column volumes of 70% ethanol, and the resulting eluent of 70% ethanol was collected, followed by vacuum concentration till no odour of alcohol can be detected. The subsequent procedures are the same as those of Example 6.

Example 22

1 g extracts of herb Astragali was dissolved in water, and diluted with water to the extent that the ratio of extracts: medicinal solution is 1:90 W:V, then 9 g β-glucosidase was added and dissolved thereinto, and then the pH of the solution was adjusted to 4.5. The mixture was allowed to undergo enzymatic hydrolysis for 48 hours at 55° C., and then filtered. The filtrate was subjected to adsorption using a 20 ml macroporous adsorption resin D101, and eluted successively with 1 column volume of water, 2 column volumes of 0.5% sodium hydroxide solution and 2 column volumes of 40% ethanol solution, and finally eluted with 2 column volumes of 70% ethanol, and the resulting eluent of 70% ethanol was collected, followed by vacuum concentration till no odour of alcohol can be detected. The subsequent procedures are the same as those of Example 6.

Example 23

3 g extracts of herb Astragali was dissolved in water, and diluted with water to the extent that the ratio of extracts: medicinal solution is 1:70 W:V, then 21 g β-glucosidase was added and dissolved thereinto, and then the pH of the solution was adjusted to 4.0. The mixture was allowed to undergo enzymatic hydrolysis for 36 hours at 50° C., and then filtered. The filtrate was subjected to adsorption using a 60 ml macroporous adsorption resin D101, and eluted successively with 1 column volume of water, 2 column volumes of 0.5% sodium hydroxide solution and 2 column volumes of 40% ethanol solution, and finally eluted with 2 column volumes of 70% ethanolt, and the resulting eluent of 70% ethanol was collected, followed by vacuum concentration till no odour of alcohol can be detected. The subsequent procedures are the same as those of Example 6.

Example 24

1 g extracts of herb Astragali was dissolved in water, and diluted with water to the extent that the ratio of extracts: medicinal solution is 1:50 W:V, then 3 g β-glucosidase was added and dissolved thereinto, and then the pH of the solution was adjusted to 5.0. The mixture was allowed to undergo enzymatic hydrolysis for 24 hours at 45° C., and then filtered. The filtrate was subjected to adsorption using a 10 ml macroporous adsorption resin D101, and eluted successively with 1 column volume of water, 2 column volumes of 0.5% sodium hydroxide solution and 2 column volumes of 40% ethanol solution, and finally eluted with 2 column volumes of 70% ethanol, and the resulting eluent of 70% ethanol was collected, is followed by vacuum concentration till no odour of alcohol can be detected. The subsequent procedures are the same as those of Example 6.

Example 25

100 g extracts of herb Astragali was dissolved in water, and diluted with water to the extent that the ratio of extracts: medicinal solution is 1:10 W:V, then 1 g β-glucosidase was added and dissolved thereinto, and then the pH of the solution was adjusted to 4.5. The mixture was allowed to undergo enzymatic hydrolysis for 48 hours at 40° C., and then filtered. The filtrate was subjected to adsorption using a 500 ml macroporous adsorption resin D101, and eluted successively with 1 column volume of water, 2 column volumes of 0.5% sodium hydroxide solution and 2 column volumes of 40% ethanol solution, and finally eluted with 2 column volumes of 70% ethanol, and the resulting eluent of 70% ethanol was collected, followed by vacuum concentration till no odour of alcohol can be detected. The subsequent procedures are the same as those of Example 6.

Example 26

70 g extracts of herb Astragali was dissolved in water, and diluted with water to the extent that the ratio of extracts: medicinal solution is 1:30 W:V, then 1 g β-glucosidase was added and dissolved thereinto, and then the pH of the solution was adjusted to 5.5. The mixture was allowed to undergo enzymatic hydrolysis for 48 hours at 50° C., and then filtered. The filtrate was subjected to adsorption using a 300 ml macroporous adsorption resin D101, and eluted successively with 1 column volume of water, 2 column volumes of 0.5% sodium hydroxide solution and 2 column volumes of 40% ethanol solution, and finally eluted with 2 column volumes of 70% ethanol, and the resulting eluent of 70% ethanol was collected, followed by vacuum concentration till no odour of alcohol can be detected. The subsequent procedures are the same as those of Example 6.

Example 27

125 ml medicinal ethanol was added to 1 g astragaloside IV to dissolve it, and the solution was added to 1800 ml water under agitation. Then 10 g exo-xylanase (with an enzyme activity of 3000 thousands U/g) were dissolved in 200 ml water, and the resulting solution was added to the above-prepared solution of astragaloside IV, and make-up water was added till total volume of the solution was 2500 ml, and then the pH of the solution was adjusted to 4.5. The mixture was allowed to undergo enzymatic hydrolysis for 12 hours at 50° C., and then filtered. The filtrate was subjected to adsorption using a 100 ml macroporous adsorption resin D101, and eluted successively with 1 column volume of water and 2 column volumes of 40% ethanol solution, and finally eluted with 2 column volumes of 70% ethanol, and the resulting eluent of 70% ethanol was collected, followed by vacuum concentration till no odour of alcohol can be detected. The subsequent procedures are the same as those of Example 6.

Example 28

0.6 g astragaloside IV was dispersed in 1800 ml water to form a suspension of astragaloside IV. Then 3 g exo-xylanase (with an enzyme activity of 5000 thousands U/g) were dissolved in 100 ml water, and the resulting solution was added to the above-prepared suspension of astragaloside IV, and make-up water was added till total volume of the solution was 2000 ml, and then the pH of the solution was adjusted to 5.0. The mixture was allowed to undergo enzymatic hydrolysis for 24 hours at 45° C., and then filtered. The subsequent procedures are the same as those of Example 27.

Example 29

0.5 g astragaloside IV was dissolved in 100 ml medicinal ethanol, and the resulting solution was added to 800 ml water under agitation. Then 10 g exo-xylanase (with an enzyme activity of 2000 thousands U/g) were dissolved in 100 ml water, and the resulting solution was added to the above-prepared solution of astragaloside IV, and then the pH of the solution was adjusted to 4.5. The mixture was allowed to undergo enzymatic hydrolysis for 48 hours at 50° C., and then filtered. The subsequent procedures are the same as those of Example 27.

Example 30

0.5 g astragaloside IV was dissolved in 50 ml medicinal ethanol, and the resulting solution was added to 400 ml water under agitation. Then 4 g exo-xylanase (with an enzyme activity of 4000 thousands U/g) were dissolved in 50 ml water, and the resulting solution was added to the above-prepared solution of astragaloside IV, and then the pH of the solution was adjusted to 4.5. The mixture was allowed to undergo enzymatic hydrolysis for 12 hours at 50° C., and then filtered. The subsequent procedures are the same as those of Example 27.

Example 31

0.2 g astragaloside IV was dissolved in 800 ml water, and 8 g exo-xylanase (with an enzyme activity of 500 thousands U/g) were dissolved in 200 ml water, and the latter solution was added to the solution of astragaloside IV, and then the pH of the resulting solution was adjusted to 4.5. The mixture was allowed to undergo enzymatic hydrolysis for 12 hours at 50° C., and then filtered. The subsequent procedures are the same as those of Example 27.

Example 32

0.8 g astragaloside IV was dissolved in 350 ml water, and 2.4 g exo-xylanase (with an enzyme activity of 5000 thousands U/g) were dissolved in 50 ml water, and the latter solution was added to the solution of astragaloside IV, and then the pH of the resulting solution was adjusted to 4.5. The mixture was allowed to undergo enzymatic hydrolysis for 12 hours at 50° C., and then filtered. The subsequent procedures are the same as those of Example 27.

Example 33

25 g extracts of Astragali was dissolved in water, and diluted with water to the extent that the ratio of extracts:medicinal solution is 1:20 W:V, then 1 g exo-xylanase (with an enzyme activity of 3000 thousands U/g) was added and dissolved thereinto, and then the pH of the solution was adjusted to 4.5. The mixture was allowed to undergo enzymatic hydrolysis for 12 hours at 50° C., and then filtered. The subsequent procedures are the same as those of Example 6.

Example 34

30 g extracts of Astragali was dissolved in water, and diluted with water to the extent that the ratio of extracts:medicinal solution is 1:10 W:V, then 2 g exo-xylanase (with an enzyme activity of 2000 thousands U/g) was added and dissolved thereinto, and then the pH of the solution was adjusted to 5. The mixture was allowed to undergo enzymatic hydrolysis for 12 hours at 50° C., and then filtered. The subsequent procedures are the same as those of Example 6.

Example 35

10 g extracts of Astragali was dissolved in water, and diluted with water to the extent that the ratio of extracts:medicinal solution is 1:40 W:V, then 0.25 g exo-xylanase (with an enzyme activity of 4000 thousands U/g) was added and dissolved thereinto, and then the pH of the solution was adjusted to 4.5. The mixture was allowed to undergo enzymatic hydrolysis for 24 hours at 45° C., and then filtered. The subsequent procedures are the same as those of Example 6.

Example 36

5 g extracts of Astragali was dissolved in water, and diluted with water to the extent that the ratio of extracts:medicinal solution is 1:80 W:V, then 5 g exo-xylanase (with an enzyme activity of 500 thousands U/g) was added and dissolved thereinto, and then the pH of the solution was adjusted to 5. The mixture was allowed to undergo enzymatic hydrolysis for 48 hours at 50° C., and then filtered. The subsequent procedures are the same as those of Example 6.

Example 37

3 g extracts of Astragali was dissolved in water, and diluted with water to the extent that the ratio of extracts:medicinal solution is 1:100 W:V, then 0.5 g exo-xylanase (with an enzyme activity of 5000 thousands U/g) was added and dissolved thereinto, and then the pH of the solution was adjusted to 4.5. The mixture was allowed to undergo enzymatic hydrolysis for 12 hours at 50° C., and then filtered. The subsequent procedures are the same as those of Example 6.

Example 38

1 g extracts of Astragali was dissolved in water, and diluted with water to the extent that the ratio of extracts:medicinal solution is 1:300 W:V, then 0.5 g exo-xylanase (with an enzyme activity of 4000 thousands U/g) was added and dissolved thereinto, and then the pH of the solution was adjusted to 5. The mixture was allowed to undergo enzymatic hydrolysis for 12 hours at 50° C., and then filtered. The subsequent procedures are the same as those of Example 6.

Example 39

0.5 g extracts of Astragali was dissolved in water, and diluted with water to the extent that the ratio of extracts:medicinal solution is 1:500 W:V, then 3 g exo-xylanase (with an enzyme activity of 5000 thousands U/g) was added and dissolved thereinto, and then the pH of the solution was adjusted to 5. The mixture was allowed to undergo enzymatic hydrolysis for 12 hours at 45° C., and then filtered. The subsequent procedures are the same as those of Example 6.

Example 40

0.3 g extracts of Astragali was dissolved in water, and diluted with water to the extent that the ratio of extracts:medicinal solution is 1:800 W:V, then 3 g exo-xylanase (with an enzyme activity of 3000 thousands U/g) was added and dissolved thereinto, and then the pH of the solution was adjusted to 5. The mixture was allowed to undergo enzymatic hydrolysis for 24 hours at 50° C., and then filtered. The subsequent procedures are the same as those of Example 6.

Example 41

0.5 g extracts of Astragali was dissolved in water, and diluted with water to the extent that the ratio of extracts:medicinal solution is 1:1000 W:V, then 4 g exo-xylanase (with an enzyme activity of 1000 thousands U/g) was added and dissolved thereinto, and then the pH of the solution was adjusted to 4.5. The mixture was allowed to undergo enzymatic hydrolysis for 48 hours at 50° C., and then filtered. The subsequent procedures are the same as those of Example 6.

Example 42

To 10 g CMG was added 40 g of a mixture of lactose:microcrystalline cellulose of 5:1 and 1% magnesium stearate. The resulting mixture was granulated with 70% ethanol and tableted to obtain 1000 tablets with a specification of 10 mg/tablet.

Example 43

0.8 g CMG and 80 g mannitol were added into 2000 ml water for injection to dissolve, and a proper amount of activated carbon was added to eliminate pyrogen therein. The resultant was filtered with a 0.2 μm microporous membrane, filled, and freeze-dried. Specification: 2 mg/vial and 5 mg/vial (in the amount of CMG). It would be dissolved in 10-20 ml water for injection, 5% glucose injection or sodium chloride injection prior to use, and then injected into an intravenous infusion solution for intravenous infusion.

Example 44

0.2 g CMG, 20 g mannitol and 5 g lactose were added into 500 ml hot water for injection to dissolve, and the resulting solution was supplemented with water to 1000 ml. A proper amount of activated carbon was added to eliminate pyrogen therein, and the resultant was filtered with a 0.2 μm microporous membrane, filled, freeze-dried, and supplied for intravenous injection use. The usage is the same as that of Example 43.

Example 45

1 g CMG, 60 g mannitol and 30 g lactose were added into 2000 ml hot water for injection to dissolve, and the resulting solution was supplemented with water to 2500 ml. A proper amount of activated carbon was added to eliminate pyrogen therein, and the resultant was filtered with a 0.2 μm microporous membrane, filled, freeze-dried, and supplied for intravenous injection use. The usage is the same as that of Example 43.

Example 46

1 g CMG, 50 g mannitol and 10 g lactose were added into 2500 ml hot water for injection to dissolve, and the resulting solution was supplemented with water to to 4000 ml. A proper amount of activated carbon was added to eliminate pyrogen therein, and the resultant was filtered with a 0.2 μm microporous membrane, filled, freeze-dried, and supplied for intravenous injection use. The usage is the same as that of Example 43.

Example 47

1 g CMG, 60 g mannitol and 10 g lactose were added into 2000 ml hot water for injection to dissolve, and the resulting solution was supplemented with water to 2500 ml. A proper amount of activated carbon was added to eliminate pyrogen therein, and the resultant was filtered with a 0.2 μm microporous membrane, filled, freeze-dried, and supplied for intravenous injection use. The usage is the same as that of Example 43.

Example 48

0.5 g CMG, 50 g mannitol and 5 g lactose were added into 2000 ml hot water for injection to dissolve, and a proper amount of activated carbon was added to eliminate pyrogen therein. The resultant was filtered with a 0.2 μm microporous membrane, filled, freeze-dried, and supplied for intravenous injection use. The usage is the same as that of Example 43.

Example 49

0.5 g CMG, 15 g mannitol and 5 g lactose were added into 1000 ml hot water for injection to dissolve, and a proper amount of activated carbon was added to eliminate pyrogen therein. The resultant was filtered with a 0.2 μm microporous membrane, filled, freeze-dried, and supplied for intravenous injection use. The usage is the same as that of Example 43.

Example 50

0.5 g CMG and 25 g lactose were added into 1000 ml hot water for injection to dissolve, and a proper amount of activated carbon was added to eliminate pyrogen therein. The resultant was filtered with a 0.2 μm microporous membrane, filled, freeze-dried, and supplied for intravenous injection use. The usage is the same as that of Example 43.

Example 51

0.4 g CMG, 40 g mannitol and 40 g lactose were added into 1000 ml hot water for injection to dissolve, and the resulting solution was supplemented with water to 2000 ml. A proper amount of activated carbon was added to eliminate pyrogen is therein, and the resultant was filtered with a 0.2 μm microporous membrane, filled, freeze-dried, and supplied for intravenous injection use. The usage is the same as that of Example 43.

Example 52

1 g CMG, 90 g mannitol and 60 g lactose were added into 2500 ml hot water for injection to dissolve, and a proper amount of activated carbon was added to eliminate pyrogen therein. The resultant was filtered with a 0.2 μm microporous membrane, filled, freeze-dried, and supplied for intravenous injection use. The usage is the same as that of Example 43.

Example 53

0.67 g CMG was dissolved while heating in 80 g ethanol that was treated with 0.3% activated carbon. 50 g dextran 40 was dissolved in 500 ml water for injection, and treated by adding 0.3% activated carbon. The above-prepared ethanol solution of CMG sample was added to the solution of dextran under agitation, and the resulting solution was supplemented with water to 1000 ml, and then filtered with a 0.2 μm microporous membrane, subpackaged and freeze-dried.

Example 54

0.67 g CMG was dissolved while heating in 16 g ethanol that was treated with 0.4% activated carbon, dispersed, and then added dropwise to 50 g polyethylene glycol 400 that was treated with activated carbon. The sample solution was added under agitation to 800 ml water solution which contained 20 g dextran 40 and 50 g mannitol and had been treated with activated carbon. The resulting solution was supplemented with water to 1000 ml, and then filtered with a 0.2 μm microporous membrane, subpackaged and freeze-dried.

Example 55

0.67 g CMG was dissolved while heating in 50 g polyethylene glycol 400 that was treated with 0.3% activated carbon. The sample solution was added under agitation to 800 ml water solution which contained 50 g mannitol and had been treated with activated carbon. The resulting solution was supplemented with water to 1000 ml, and then filtered with a 0.2 μm microporous membrane, subpackaged and freeze-dried.

Example 56

0.67 g CMG was dissolved while heating in 50 g propanediol that was treated with 0.3% activated carbon. The sample solution was added under agitation to 800 ml water solution which contained 50 g mannitol and had been treated with activated carbon. The resulting solution was supplemented with water to 1000 ml, and then filtered with a 0.2 μm microporous membrane, subpackaged and freeze-dried.

Example 57

0.5 g CMG was dissolved while heating in 50 g polyethylene glycol 400 that was treated with 0.3% activated carbon. The sample solution was added under agitation to 800 ml water solution which contained 25 g mannitol and had been treated with activated carbon. The resulting solution was supplemented with water to 1000 ml, and then filtered with a 0.2 μm microporous membrane, subpackaged and freeze-dried.

Example 58

0.5 g CMG was dissolved while heating in 30 g polyethylene glycol 400 that was treated with 0.3% activated carbon. The sample solution was added under agitation to 800 ml water solution which contained 60 g mannitol and had been treated with activated carbon. The resulting solution was supplemented with water to 1000 ml, and then filtered with a 0.4 μm microporous membrane, subpackaged and freeze-dried.

Example 59

0.6 g CMG was dissolved while heating in 60 g ethanol that was treated with 0.3% activated carbon, and the resulting solution was added dropwise into 10 g polyethylene glycol 400 that was treated with activated carbon. The sample solution was added under agitation to 800 ml water solution which contained 50 g mannitol and had been treated with activated carbon. The resulting solution was supplemented with water to 1000 ml, and then filtered with a 0.2 μm microporous membrane, subpackaged and freeze-dried.

Example 60

0.5 g CMG was dissolved while heating in 60 g ethanol that was treated with 0.3% activated carbon, and the resulting solution was added dropwise into 10 g polyethylene glycol 400 that was treated with activated carbon. The sample solution was added under agitation to 800 ml water solution which contained 15 g mannitol and had been treated with activated carbon. The resulting solution was supplemented with water to 1000 ml, and then filtered with a 0.2 μm microporous membrane, subpackaged and freeze-dried.

Example 61

0.5 g CMG was dissolved while heating in 60 g ethanol that was treated with 0.3% activated carbon, and the resulting solution was added dropwise into 10 g polyethylene glycol 400 that was treated with activated carbon. The sample solution was added under agitation to 800 ml water solution which contained 30 g mannitol and had been treated with activated carbon. The resulting solution was supplemented with water to 1000 ml, and then filtered with a 0.2 μm microporous membrane, subpackaged and freeze-dried.

Example 62

To 10 g CMG were added 10 g dextrin and 30 g lactose, and the resulting mixture was granulated with 60% ethanol, and then dried and encapsulated to obtain 1000 capsules.

Example 63

1 g CMG and 125 g glucose were added into 2000 ml hot water for injection to dissolve, and the resulting solution was supplemented with water for injection to 2500 ml, and then adjusted to isotonicity. A proper amount of activated carbon was added to eliminate pyrogen therein, and the resultant was filtered with a 0.2 μm microporous membrane and filled to produce vial injections.

Example 64

0.8 g CMG and 18 g sodium chloride were added into 2000 ml hot water for injection to dissolve, and the resulting solution was supplemented with water for injection to 4000 ml, and then adjusted to isotonicity. A proper amount of activated carbon was added to eliminate pyrogen therein, and the resultant was filtered with a 0.2 μm microporous membrane and filled to produce vial injections.

Example 65

0.6 g CMG and 10 g glucose were added into 1500 ml hot water for injection to dissolve, and the resulting solution was supplemented with water for injection to 2000 ml, and then adjusted to isotonicity. A proper amount of activated carbon was added to eliminate pyrogen therein, and the resultant was filtered with a 0.2 μm microporous membrane and filled to produce vial injections.

Example 66

0.6 g CMG was added into 50 ml propanediol to dissolve, and the resulting solution was supplemented with water for injection to 1000 ml, and then adjusted to isotonicity. A proper amount of activated carbon was added to eliminate pyrogen therein, and then filtered with a 0.2 μm microporous membrane and filled to produce vial injections.

Example 67

0.1 g CMG was added into 500 ml hot water for injection to dissolve, and the resulting solution was supplemented with water for injection to 1000 ml, and then adjusted to isotonicity. A proper amount of activated carbon was added to eliminate pyrogen therein, and then filtered with a 0.2 μm microporous membrane and filled to produce vial injections.

Example 68

0.4 g CMG was added into 100 ml ethanol to dissolve, and the resulting solution was supplemented with water for injection to 500 ml, and then adjusted to isotonicity. A proper amount of activated carbon was added to eliminate pyrogen therein, and then filtered with a 0.2 μm microporous membrane and filled to is produce vial injections.

Example 69

1 g CMG, 50 g glucose, 10 g sorbitol and 300 ml ethanol was used. The CMG was firstly dissolved in a prescribed amount of ethanol, and the resulting solution was diluted by adding 200 ml water for injection, and then a prescribed amount of glucose and sorbitol was added and dissolved therein. The resultant was supplemented with water for injection to 1000 ml, and a proper amount of activated carbon was added to eliminate pyrogen therein. The resultant was filtered with a 0.2 μm microporous membrane and filled to produce vial injections.

Example 70

1 g CMG, 50 g glucose, 10 g sorbitol and 200 ml propanediol was used. The CMG was firstly dissolved in a prescribed amount of propanediol, and the resulting solution was diluted by adding 100 ml water for injection, and then a prescribed amount of glucose and sorbitol was added and dissolved therein. The resultant was supplemented water for injection to 500 ml, and a proper amount of activated carbon was added to eliminate pyrogen therein. The resultant was filtered with a 0.2 μm microporous membrane and filled to produce vial injections.

Example 71

1 g CMG was dissolved in 60 ml ethanol, and the resulting solution was supplemented with water for injection to 100 ml, and a proper amount of activated carbon was added to eliminate pyrogen therein. The resultant was filtered with a 0.2 μm microporous membrane and filled to produce vial injections.

Example 72

0.8 g CMG was dissolved in 30 ml ethanol, and 20 ml propanediol was added and mixed until homogeneity was achieved. The resulting solution was supplemented with water for injection to 100 ml, and a proper amount of activated carbon was added to eliminate pyrogen therein. The resultant was filtered with a 0.2 μm microporous membrane and filled to produce vial injections.

Example 73

0.8 g CMG was dissolved in 60 ml ethanol, and 30 ml propanediol was added and mixed until homogeneity was achieved. The resulting solution was supplemented with water for injection to 200 ml, and a proper amount of activated carbon was added to eliminate pyrogen therein. The resultant was filtered with a 0.2 μm microporous membrane and filled to produce vial injections.

Example 74

1 g CMG and 1000 g glucose were dissolved in 3 L water for injection while heating, and the resulting solution was supplemented with water for injection to 20 L, and then the pH of the solution was adjusted to 6.5. A proper amount of activated carbon was added to eliminate pyrogen therein, and the resultant was filtered with a 0.2 μm microporous membrane and filled to produce infusions. Specifications: 100 ml/bottle, 250 ml/bottle and 500 ml/bottle.

Example 75

0.8 g CMG and 180 g sodium chloride were added into 3 L hot water for injection to dissolve, and the resulting solution was supplemented with water for injection to 20 L, and then the pH of the solution was adjusted to 7.0. A proper amount of activated carbon was added to eliminate pyrogen therein, and the resultant was filtered with a 0.2 μm microporous membrane and filled to produce infusions. Specifications: 100 ml/bottle and 250 ml/bottle.

Example 76

2 g CMG and 1000 g glucose were added into 5 L hot water for injection to dissolve, and the resulting solution was supplemented with water for injection to 20 L, and then the pH of the solution was adjusted to 7.0. A proper amount of activated carbon was added to eliminate pyrogen therein, and the resultant was filtered with a 0.2 μm microporous membrane and filled to produce infusions. Specifications: 100 ml/bottle and 250 ml/bottle.

Example 77

2 g CMG and 500 g glucose were added into 5 L hot water for injection to dissolve, and the resulting solution was supplemented with water for injection to 10 L, and then the pH of the solution was adjusted to 7.0. A proper amount of activated carbon was added to eliminate pyrogen therein, and the resultant was filtered with a 0.2 μm microporous membrane and filled to produce infusions. Specifications: 100 ml/bottle, 250 ml/bottle and 500 ml/bottle.

Example 78

0.4 g CMG and 1000 g glucose were added into 5 L hot water for injection to dissolve while heating, and the resulting solution was supplemented with water for injection to 20 L, and then the pH of the solution was adjusted to 7.0. A proper amount of activated carbon was added to eliminate pyrogen therein, and the resultant was filtered with a 0.2 μm microporous membrane and filled to produce infusions. Specifications: 100 ml/bottle, 250 ml/bottle and 500 ml/bottle.

Example 79

0.8 g CMG and 1000 g glucose were added into 5 L hot water for injection to dissolve while heating, and the resulting solution was supplemented with water for injection to 10 L, and then the pH of the solution was adjusted to 6.0. A proper amount of activated carbon was added to eliminate pyrogen therein, and the resultant was filtered with a 0.2 μm microporous membrane and filled to produce infusions. Specifications: 100 ml/bottle, 250 ml/bottle and 500 ml/bottle.

Example 80

1 g CMG and 100 g glucose were added into 500 ml water for injection to dissolve while heating, and the resulting solution was supplemented with water for injection to 2000 ml, and then the pH of the solution was adjusted to 6.5. A proper amount of activated carbon was added to eliminate pyrogen therein, and the resultant was filtered with a 0.2 μm microporous membrane and filled to produce infusions. Specifications: 100 ml/bottle, 250 ml/bottle and 500 ml/bottle.

Example 81

0.1 g CMG and 500 g glucose were added into 5 L water for injection to dissolve is while heating, and the resulting solution was supplemented with water for injection to 10 L, and then the pH of the solution was adjusted to 7.5. A proper amount of activated carbon was added to eliminate pyrogen therein, and the resultant was filtered with a 0.2 μm microporous membrane and filled to produce infusions. Specifications: 100 ml/bottle, 250 ml/bottle and 500 ml/bottle.

Example 82

5 g CMG, 50 g PEG6000 and a proper amount of 95% ethanol were used. A prescribed amount of CMG was taken and dissolved in a proper amount of ethanol, and the resulting solution was heated with water bath and added to molten PEG6000. The resultant was added dropwise while holding its temperature at 50° C. into a liquid paraffin coolant at a temperature of 10° C. to condense into pills so as to obtain pills.

Example 83

5 g CMG, 50 g poloxamer and a proper amount of 95% ethanol were used. A prescribed amount of CMG was taken and dissolved in a proper amount of ethanol, and the resulting solution was added to molten poloxamer. The resultant was added dropwise while stirring and holding the temperature into cooled dimethicone so as to produce pills.

Our studies revealed that the pharmacological activities of CMG are equivalent to those of astragaloside IV, but the solubility thereof are significantly improved (astragaloside IV: 2-4 mg/100 ml; CMG: 40-50 mg/100 ml), and that CMG possesses good oral absorption properties and thus has the potentiality of being developed as drugs.

Example 84

Cardiotonic Effects of CMG on Isolated Heart

Methods:

Wistar rats (250-280 g) were anesthetized with chloral hydrate (360 mg/kg intraperitoneally) and heparinized with sodium heparin (1 mg) via sublingual vein. After opening the chest cavity, the hearts were quickly excised and immersed in cold Krebs-Henseleit (K-H) solution. Hearts were retrogradely perfused with 74 centimeters of water pressure via the aorta in a Langendorff apparatus with K-H solution, which was bubbled with a mixture of 95% $O_2$ and 5% $CO_2$. The suture fixed on cardiac apex was connected to a tension transducer which was connected to a polygraph (RM6300, Nihon Kohden, Japan) and a data acquisition workstation (MP150, BIOPAC Systems, USA) to a computer running Acknowledge (version 3.7.1).

Results:

1. The Effects of CMG on Heart Rate (HR)

Heart rate decreased in both CMG and astragaloside IV groups, and there was no significant difference between those two groups (Table 1).

2. The Effects of CMG on Contractility

Contractility increased in both CMG and astragaloside IV groups, and there was no significant difference between those two groups (Table 2).

TABLE 1

The effects of CMG on HR (bpm)

| Groups | Concentration (mol/L) | n | Before administration | After administration | Variation (%) |
|---|---|---|---|---|---|
| Control | — | 9 | 149 ± 46 | 141 ± 40 | −5 ± 14 |
| astragaloside IV | $1 \times 10^{-8}$ | 5 | 152 ± 30 | 144 ± 34 | −6 ± 5 |
|  | $3 \times 10^{-8}$ | 5 | 167 ± 64 | 145 ± 65 | −14 ± 13 |
|  | $1 \times 10^{-7}$ | 5 | 151 ± 60 | 117 ± 52* | −24 ± 17+ |
| CMG | $1 \times 10^{-8}$ | 6 | 156 ± 51 | 124 ± 25 | −17 ± 18 |
|  | $3 \times 10^{-8}$ | 5 | 150 ± 41 | 128 ± 23 | −13 ± 12 |
|  | $1 \times 10^{-7}$ | 5 | 145 ± 16 | 92 ± 35* | −38 ± 22++ |
| AD | $1 \times 10^{-8}$ | 5 | 137 ± 38 | 227 ± 40** | 70 ± 21+++ |

Note:
1. *$P < 0.05$, **$P < 0.001$ vs before administration;
2. +$P < 0.05$, ++$P < 0.01$, +++$P < 0.001$ vs control.

TABLE 2

The effects of CMG on contractility (g)

| Groups | Concentration (mol/L) | n | Contractility | | |
|---|---|---|---|---|---|
|  |  |  | Before administration | After administration | Variation (%) |
| Control | — | 9 | 1.93 ± 0.91 | 1.82 ± 0.75 | −2.59 ± 12.63 |
| astragaloside IV | $1 \times 10^{-8}$ | 5 | 1.83 ± 0.38 | 1.94 ± 0.43 | 6.00 ± 9.25 |
|  | $3 \times 10^{-8}$ | 5 | 1.78 ± 0.46 | 1.88 ± 0.40 | 6.98 ± 8.82 |
|  | $1 \times 10^{-7}$ | 5 | 1.42 ± 0.41 | 1.73 ± 0.42** | 24.56 ± 12.44++ |
| CMG | $1 \times 10^{-8}$ | 6 | 1.81 ± 0.49 | 1.97 ± 0.61 | 7.72 ± 8.03 |
|  | $3 \times 10^{-8}$ | 5 | 1.83 ± 0.72 | 1.92 ± 0.72 | 5.84 ± 2.92 |
|  | $1 \times 10^{-7}$ | 5 | 1.77 ± 0.52 | 2.06 ± 0.59** | 17.08 ± 7.19++ |
| AD | $1 \times 10^{-8}$ | 5 | 1.56 ± 0.61 | 1.72 ± 0.64** | 11.22 ± 4.19+ |

Note:
1. *$P < 0.05$, **$P < 0.01$ vs before administration;
2. +$P < 0.05$, ++$P < 0.01$ vs control.

3. The Effects of CMG on Peak Derivatives of Contractility

Peak derivatives of contractility in CMG and astragaloside IV groups increased, and there was no significant difference between those two groups (Table 3).

TABLE 3

The Effects of CMG on peak derivatives of contractility (g/s)

| Groups | Concentration (mol/L) | n | Δ T/S | | |
|---|---|---|---|---|---|
|  |  |  | before administration | after administration | Variation (%) |
| Control | — | 9 | 74 ± 16 | 72 ± 17 | −3 ± 12 |
| astragaloside IV | $1 \times 10^{-8}$ | 5 | 76 ± 18 | 81 ± 19 | 6 ± 15 |
|  | $3 \times 10^{-8}$ | 5 | 69 ± 19 | 76 ± 18** | 12 ± 7+ |
|  | $1 \times 10^{-7}$ | 5 | 66 ± 13 | 78 ± 14* | 21 ± 19+ |
| CMG | $1 \times 10^{-8}$ | 6 | 71 ± 15 | 76 ± 19 | 6 ± 8 |
|  | $3 \times 10^{-8}$ | 5 | 70 ± 16 | 77 ± 16* | 11 ± 9+ |
|  | $1 \times 10^{-7}$ | 5 | 73 ± 11 | 86 ± 13** | 18 ± 6++ |
| AD | $1 \times 10^{-8}$ | 5 | 69 ± 20 | 77 ± 24* | 13 ± 4+ |

Note:
1. *$P < 0.05$, **$P < 0.01$ vs before administration;
2. +$P < 0.05$, +++$P < 0.001$ vs control.

4. The Effects of CMG on Peak Derivatives of Diastolic Force

Peak derivatives of diastolic force in CMG and astragaloside IV groups increased, and there was no significant difference between those two groups (Table 4).

TABLE 4

The effects of CMG on peak derivatives of diastolic force (g/s)

| Groups | Concentration (mol/L) | n | Δ T/S before administration | after administration | Variation (%) |
|---|---|---|---|---|---|
| Control | — | 9 | −43 ± 11 | −42 ± 13 | −2 ± 13 |
| astragaloside IV | 1 × 10⁻⁸ | 5 | −43 ± 10 | −46 ± 9 | 8 ± 8 |
|  | 3 × 10⁻⁸ | 5 | −41 ± 12 | −45 ± 12 | 10 ± 11 |
|  | 1 × 10⁻⁷ | 5 | −44 ± 11 | −50 ± 11* | 15 ± 9⁺ |
| CMG | 1 × 10⁻⁸ | 6 | −44 ± 15 | −47 ± 16 | 7 ± 9 |
|  | 3 × 10⁻⁸ | 5 | −46 ± 15 | −51 ± 18 | 10 ± 8 |
|  | 1 × 10⁻⁷ | 5 | −45 ± 14 | −51 ± 14* | 14 ± 8⁺ |
| AD | 1 × 10⁻⁸ | 5 | −41 ± 9 | −53 ± 13** | 28 ± 9⁺⁺⁺ |

Note:
1. *$P < 0.05$, **$P < 0.01$ vs before administration;
2. ⁺$P < 0.05$, ⁺⁺⁺$P < 0.001$ vs control.

Conclusions: CMG exhibited cardiotonic effects on an isolated rat heart, and the effects of CMG were equivalent to those of astragaloside IV.

Example 85

Effects of CMG on Hemodynamics of Anesthetized Open-Chest Dogs

1. Purpose of the Experiment

The purpose of the experiment was to observe the influence of CMG (intravenously) on various indexes of cardiac function compared with astragaloside IV in anesthetized open-chest dogs, which could provide an experimental basis for further investigation of CMG.

2. Experimental Materials 2.1 Medicines and Preparations (1) CMG injection: a colorless transparent liquid, 0.35 mg·mL⁻¹, lot: 041230, provided by the Innovation Center of Tianjin Institute of Pharmaceutical Research. (2) Astragaloside IV injection: a colorless transparent liquid, 1.5 mg·mL⁻¹, lot: 040323, provided by the Innovation Center of Tianjin Institute of Pharmaceutical Research.

2.2 Experimental Animals

Adult healthy mongrel dogs were purchased from the suburbs of Tianjin.

2.3 Experimental Instruments (1) Model RM-6300 8-channel physiological recorder (Nihon Kohden, Japan);

(2) Model MFV-3200 electromagnetic blood flowmeter (Nihon Kohden Japan);

(3) Model MP-100 data acquisition workstation (BIOPAC Systems, USA)

(4) Model SC-3 electric respirator (Fourth Medical Equipment Factory, Shanghai, China).

3. Experimental Methods

The animals were anesthetized by intravenous injection of 30 mg/kg sodium pentobarbital, tracheally intubated, and mechanically ventilated with positive air pressure. Left thoracotomy was performed through the fourth intercostal space and the heart was suspended in a pericardial cradle, the aortic root was isolated and a probe of blood flow meter (12 or 14 mm in diameter) was fixed to measure the aortic blood flow as a representation of cardiac output (CO), the circumflex branch of left coronary artery was isolated and a probe of blood flow meter (2 or 2.5 mm in diameter) was fixed to measure the coronary blood flow (CBF). A polyethylene catheter filled with heparin physiological saline was inserted through cardiac apex into the left ventricle to measure the left ventricular pressure (LVP) and left ventricular end-diastolic pressure (LVEDP), Peak positive and peak negative first derivatives of the LVP (+ LVdp/dt and − LVdp/dt) were calculated with the Acknowledge software. The systolic blood pressure (SBP), diastolic blood pressure (DBP) and mean arterial pressure (MAP) were measured by polyethylene catheter via the femoral artery, ECG □ was measured by a AC-601G ECG amplifier. The above-mentioned analog signal was input into a data acquisition workstation (MP100, BIOPAC Systems, USA) to a computer running Acknowledge (version 3.7.1).

After surgery, various indexes before administration were recorded until the indexes were stable, and then intravenous infusion administration was conducted. Thirty dogs were divided into five groups (six dogs in each group), the experiment groups were given 0.15, 0.3, 0.6 mg/kg of ASP-□ respectively, the normal control group was given 1 ml/kg of solvent, and the positive control group was given 0.3 mg/kg of astragaloside IV. The delivery volumes were 15 ml for each dog was and the delivery velocity was 1 ml/min. The indexes were recorded at 5, 10, 15, 20, 30, 45, 60, 90 and 120 mins after drug administration. At the end of experiment, the hearts were excised and weighted. The myocardial blood flow for per hectogram (CF), coronary resistance (CR), cardiac index (CI), left ventricular work (LVW) and total peripheral resistance (TPR) were calculated according to the following formulae:

CF=CBF×300/heart weight

CR=MAP/CF

CI=CO/0.11×(body weight)²/³

LVW=CO×(MAP−5)×1.052×0.0136

TPR=MAP×79.92/CO

Data are expressed as mean±SD ($\bar{x}$±s), the paired t-test was used to compare the significance between before and after administration, the unpaired t-test was adopted for comparison between groups.

4. Experimental Results 4.1 The Effects of CMG on Blood Pressure and Heart Rate

There were no significant changes in SBP, DBP, MAP and HR within 120 min after administration of CMG in dose of 0.15, 0.3 and 0.6 mg/kg. There was no significant change in blood pressure after administration of astragaloside IV in comparison with pre-administration, whereas heart rate decreased slightly. There was no significant difference between equal dosage (0.3 mg/kg) of CMG and astragaloside IV.

4.2 The Effects of CMG on Left Ventricular Function (Tables 5 and 6)

There were no significant changes in LVP, LVEDP, LVW, ±LVdp/dt$_{max}$ on the anesthetized open-chest dogs within 120 min after administration of control solvent.

LVP: After intravenous administration of CMG in dose of 0.15, 0.3 and 0.6 mg/kg, there was no significant change in left ventricular pressure within 120 min.

LVEDP: After administration of CMG in dose of 0.15, 0.3 and 0.6 mg/kg, the LVEDP decreased dose-dependently, and LVEDP maximumly decreased by 1.1±0.4, 1.5±0.8, 2.1±0.5 mmHg (P<0.01) respectively, and the effects lasted for more than 2 hours.

LVW: There was no significant change in left ventricular work after administration of CMG in an amount of 0.15, 0.3 and 0.6 mg/kg.

±LVdp/dt$_{max}$: There was no significant change in ±LVdp/dt$_{max}$ within 120 min after administration of CMG in dose of 0.15 mg/kg. +LVdp/dt$_{max}$ maximumly increased by 12.0±5.0 and 22.6±11.8% (P<0.01) respectively at 5-10 min after administration of CMG in dose of 0.3 and 0.6 mg/kg, and there was no significant effect on −LVdp/dt$_{max}$.

There was no significant change in LVSP, LVW and −LVdp/dt$_{max}$ after administration of astragaloside IV, and +LVdp/dt$_{max}$ significantly increased whereas LVEDP significantly decreased. There was no significant difference between equal dosage (0.3 mg/kg) of CMG and astragaloside IV.

4.3 The Effects of CMG on Cardiac Pumping Function and Total Peripheral Resistance (Table 7)

There were no significant changes in CO, CI and TPR on the anesthetized open-chest dogs within 120 min after intravenous administration of physiological saline.

CO and CI: After intravenous administration of CMG in dose of 0.15, 0.3 and 0.6 mg/kg, there were no significant changes in CO and CI within 120 min, TPR: After intravenous administration of CMG in dose of 0.15, 0.3 and 0.6 mg/kg, there was no significant change in total peripheral resistance within 120 min.

Astragaloside IV as control medicine has no significant effect on CO, CI and TPR, and shows no significant difference with CMG in an equal dosage.

4.4 The Effects on Coronary Blood Flow and Coronary Resistance (Table 8)

There were no significant changes in CF and CR on the anesthetized open-chest dogs within 120 min after intravenous administration of physiological saline.

There were no significant changes in CF and CR within 120 min after antravenous administration of CMG in dose of 0.15, 0.3 and 0.6 mg/kg.

There were no significant changes in CF and CR within 120 min after antravenous administration of astragaloside IV.

CONCLUSIONS

There were no significant changes in all hemodynamic indexes except LVEDP after administration of 0.15 mg/kg CMG in single time; as for 0.3 and 0.6 mg/kg, LVEDP significantly decreased, +LVdp/dt$_{max}$ increased, and no significant change occurred for other hemodynamic indexes. The control medicine of astragaloside IV significantly decreased LVEDP and enhanced +LVdp/dt$_{max}$, and its effects on various indexes of anesthetized open-chest dogs have no significant difference compared to that of CMG in an equal dosage.

CMG can effectively improve the hemodynamic indexes on anesthetized dogs, and CMG has equivalent effect on hemodynamic indexes with astragaloside IV in an equal dosage.

TABLE 5

The Effects of Intravenous Administration of CMG on LVP and LVW on Anesthetized Open-Chest Dogs ($\bar{x}$ ± s, n = 6)

| Index | Groups | Dosage (mg/kg) | Before administration | After administration (min) | | | |
|---|---|---|---|---|---|---|---|
| | | | | 5 | 10 | 15 | 20 |
| LVP mmHg | Control | — | 109 ± 30 | 110 ± 32 (1.3 ± 10.2) | 108 ± 32 (−0.6 ± 7.8) | 107 ± 37 (−1.7 ± 12.9) | 108 ± 32 (−1.1 ± 4.8) |
| | CMG | 0.15 | 105 ± 22 | 105 ± 21 (0.1 ± 3.4) | 103 ± 22 (−1.5 ± 3.7) | 103 ± 25 (−2.0 ± 4.7) | 101 ± 21 (−3.8 ± 5.1) |
| | CMG | 0.3 | 103 ± 20 | 107 ± 21 (4.1 ± 4.9) | 106 ± 22 (2.3 ± 6.9) | 106 ± 20 (2.3 ± 5.4) | 104 ± 23 (1.2 ± 6.9) |
| | CMG | 0.6 | 106 ± 16 | 105 ± 14 (−1.1 ± 3.5) | 105 ± 17 (−1.3 ± 5.0) | 105 ± 17 (−0.8 ± 4.1) | 107 ± 17 (0.4 ± 3.9) |
| | Astragaloside IV | 0.3 | 103 ± 12 | 104 ± 10 (1.1 ± 6.5) | 105 ± 10 (2.5 ± 11.7) | 103 ± 12 (−0.3 ± 12.2) | 104 ± 11 (1.2 ± 16.2) |
| LVEDP mmHg | Control | — | 2.5 ± 1.0 | 2.4 ± 0.8 (−0.06 ± 0.44) | 2.4 ± 1.1 (−0.07 ± 0.87) | 2.6 ± 0.8 (0.13 ± 0.29) | 2.2 ± 0.8 (−0.3 ± 0.44) |
| | CMG | 0.15 | 1.8 ± 2.2 | 1.0 ± 2.3* (−0.78 ± 0.61) | 1.0 ± 2.3* (−0.73 ± 0.49) | 1.0 ± 2.3* (−0.73 ± 0.60) | 1.2 ± 2.4* (−0.62 ± 0.47) |
| | CMG | 0.3 | 1.7 ± 2.2 | 1.3 ± 2.5 (−0.39 ± 0.38) | 1 ± 2.4** (−0.75 ± 0.34) | 0.7 ± 2.6** (−1.06 ± 0.54) | 0.6 ± 2.5* (−1.16 ± 0.89) |
| | CMG | 0.6 | 2.7 ± 1.3 | 1.5 ± 1.6* (−1.17 ± 0.78) | 0.9 ± 1.6** (−1.74 ± 0.68) | 1.3 ± 1.6** (−1.38 ± 0.51) | 1.2 ± 1.6** (−1.5 ± 0.54) |
| | Astragaloside IV | 0.3 | 2.4 ± 1.1 | 1.6 ± 1.4 (−0.80 ± 0.81) | 1.7 ± 1.3* (−0.73 ± 0.54) | 1.0 ± 1.2** (−1.40 ± 0.54) | 1.0 ± 1.1** (−1.46 ± 0.68) |
| LVW kg · m | Control | — | 1.13 ± 0.51 | 1.29 ± 0.62 (0.16 ± 0.21) | 1.19 ± 0.58 (0.06 ± 0.12) | 1.15 ± 0.58 (0.02 ± 0.11) | 1.22 ± 0.56 (0.09 ± 0.12) |
| | CMG | 0.15 | 1.12 ± 0.42 | 1.15 ± 0.43 (0.03 ± 0.17) | 1.18 ± 0.34 (0.06 ± 0.19) | 1.08 ± 0.31 (−0.04 ± 0.19) | 1.04 ± 0.23 (−0.08 ± 0.21) |
| | CMG | 0.3 | 1.02 ± 0.47 | 1.12 ± 0.49* (0.10 ± 0.07) | 1.02 ± 0.44 (0.00 ± 0.15) | 1.02 ± 0.44 (0.00 ± 0.16) | 1.02 ± 0.47 (0.00 ± 0.05) |
| | CMG | 0.6 | 1.08 ± 0.41 | 1.11 ± 0.38 (0.03 ± 0.11) | 1.11 ± 0.34 (0.03 ± 0.15) | 1.14 ± 0.41 (0.06 ± 0.13) | 1.13 ± 0.35 (0.06 ± 0.17) |
| | Astragaloside | 0.3 | 1.21 ± 0.44 | 1.22 ± 0.47 | 1.26 ± 0.39 | 1.22 ± 0.35 | 1.2 ± 0.31 |

TABLE 5-continued

The Effects of Intravenous Administration of CMG on LVP and LVW on Anesthetized Open-Chest Dogs ($\bar{x} \pm s$, n = 6)

| Index | Groups | Dosage (mg/kg) | Before administration | After administration (min) | | | | |
|---|---|---|---|---|---|---|---|---|
| | | | | 30 | 45 | 60 | 90 | 120 |
| | IV | | | (0.01 ± 0.05) | (0.05 ± 0.13) | (0.01 ± 0.16) | (−0.01 ± 0.22) | |
| LVP mmHg | Control | — | 109 ± 30 | 108 ± 26 (−1.1 ± 5.8) | 109 ± 25 (0.0 ± 11.9) | 101 ± 19 (−7.2 ± 13.6) | 101 ± 26 (−7.8 ± 22.0) | 101 ± 26 (−7.5 ± 19.9) |
| | CMG | 0.15 | 105 ± 22 | 100 ± 21 (−5.0 ± 7.3) | 101 ± 19 (−3.6 ± 4.6) | 101 ± 19 (−4.1 ± 4.9) | 101 ± 18 (−3.5 ± 7.6) | 103 ± 22 (−1.8 ± 8.1) |
| | CMG | 0.3 | 103 ± 20 | 102 ± 23 (−1.3 ± 4.7) | 98 ± 22 (−4.8 ± 5.5) | 98 ± 22 (−5.7 ± 6.0) | 99 ± 20 (−4.5 ± 7.0) | 100 ± 23 (−3.5 ± 10.3) |
| | CMG | 0.6 | 106 ± 16 | 107 ± 17 (0.9 ± 5.6) | 106 ± 16 (0.2 ± 5.2) | 105 ± 14 (−0.8 ± 7.7) | 105 ± 12 (−1.3 ± 6.7) | 102 ± 17 (−4.4 ± 5.9) |
| | Astragaloside IV | 0.3 | 103 ± 12 | 102 ± 11 (−0.7 ± 13.7) | 98 ± 10 (−4.5 ± 11.7) | 98 ± 11 (−5.3 ± 15.3) | 99 ± 15 (−4.2 ± 18.7) | 97 ± 14 (−5.5 ± 19.3) |
| LVEDP mmHg | Control | — | 2.5 ± 1.0 | 2.3 ± 1.2 (−0.24 ± 0.86) | 2.5 ± 1.1 (−0.03 ± 0.29) | 2.5 ± 1.0 (0.03 ± 0.84) | 2.8 ± 0.8 (0.27 ± 0.38) | 2.4 ± 0.9 (−0.07 ± 0.24) |
| | CMG | 0.15 | 1.8 ± 2.2 | 1.2 ± 2.4* (−0.58 ± 0.46) | 1.3 ± 2.2* (−0.5 ± 0.44) | 1.3 ± 2.1* (−0.46 ± 0.41) | 1.4 ± 2.4 (−0.40 ± 0.43) | 1.6 ± 2.3 (−0.15 ± 0.44) |
| | CMG | 0.3 | 1.7 ± 2.2 | 0.6 ± 2.4* (−1.11 ± 0.87) | 0.5 ± 2.3** (−1.28 ± 0.75) | 0.8 ± 2.8* (−0.98 ± 0.88) | 0.9 ± 2.6* (−0.83 ± 0.72) | 1.0 ± 2.1* (−0.71 ± 0.45) |
| | CMG | 0.6 | 2.7 ± 1.3 | 1.3 ± 1.5** (−1.4 ± 0.6) | 1.3 ± 1.7** (−1.41 ± 0.81) | 1.6 ± 1.6* (−1.05 ± 0.76) | 1.3 ± 1.4** (−1.35 ± 0.72) | 2.0 ± 1.2* (−0.73 ± 0.52) |
| | Astragaloside IV | 0.3 | 2.4 ± 1.1 | 1.0 ± 1.4* (−1.44 ± 0.90) | 0.9 ± 2.1* (−1.55 ± 1.42) | 0.8 ± 1.7* (−1.57 ± 1.39) | 1.4 ± 0.5* (−0.97 ± 0.77) | 1.8 ± 0.8* (−0.66 ± 0.47) |
| LVW kg·m | Control | — | 1.13 ± 0.51 | 1.14 ± 0.50 (0.01 ± 0.11) | 1.19 ± 0.56 (0.06 ± 0.17) | 1.14 ± 0.64 (0.01 ± 0.16) | 1.16 ± 0.64 (0.02 ± 0.25) | 1.22 ± 0.66 (0.09 ± 0.25) |
| | CMG | 0.15 | 1.12 ± 0.42 | 1.01 ± 0.26 (−0.11 ± 0.27) | 1.06 ± 0.31 (−0.06 ± 0.32) | 1.00 ± 0.34 (−0.12 ± 0.33) | 0.96 ± 0.24 (−0.16 ± 0.34) | 0.99 ± 0.36 (−0.13 ± 0.37) |
| | CMG | 0.3 | 1.02 ± 0.47 | 0.97 ± 0.46 (−0.05 ± 0.13) | 1.00 ± 0.48 (−0.02 ± 0.11) | 0.90 ± 0.43 (−0.12 ± 0.26) | 0.90 ± 0.53 (−0.12 ± 0.32) | 0.94 ± 0.54 (−0.08 ± 0.37) |
| | CMG | 0.6 | 1.08 ± 0.41 | 1.15 ± 0.45 (0.07 ± 0.13) | 1.1 ± 0.29 (0.03 ± 0.23) | 1.17 ± 0.40 (0.10 ± 0.20) | 1.17 ± 0.44 (0.10 ± 0.11) | 1.12 ± 0.42 (0.04 ± 0.18) |
| | Astragaloside IV | 0.3 | 1.21 ± 0.44 | 1.19 ± 0.40 (−0.02 ± 0.15) | 1.14 ± 0.40 (−0.07 ± 0.11) | 1.16 ± 0.47 (−0.05 ± 0.09) | 1.14 ± 0.44 (−0.07 ± 0.08) | 1.17 ± 0.45 (−0.04 ± 0.05) |

Note:
1. *$p < 0.05$, **$p < 0.01$ vs before administration in paired comparisons;
2. Numbers in brackets were the changes compared to before administration;
3. There was no significant difference between equal dosage of CMG and astragaloside IV.

TABLE 6

The Effects of Intravenous Administration of CMG on Maximum Left Ventricular Change Rate on Anesthetized Open-Chest Dogs ($\bar{x} \pm s$, n = 6)

| Index | Groups | Dosage (mg/kg) | Before administration | After administration (min) | | | |
|---|---|---|---|---|---|---|---|
| | | | | 5 | 10 | 15 | 20 |
| dp/dt mmHg/s | Control | — | 1288 ± 577 | 1360 ± 690 (73 ± 140) | 1284 ± 630 (−4 ± 101) | 1285 ± 627 (−3 ± 152) | 1318 ± 643 (30 ± 114) |
| | CMG | 0.15 | 1150 ± 391 | 1205 ± 417 (56 ± 94) | 1173 ± 407 (23 ± 110) | 1170 ± 449 (20 ± 113) | 1144 ± 452 (−6 ± 113) |
| | CMG | 0.3 | 1261 ± 453 | 1308 ± 448* (47 ± 34) | 1358 ± 444* (97 ± 68) | 1367 ± 470** (106 ± 54) | 1348 ± 487* (87 ± 77) |
| | CMG | 0.6 | 1104 ± 295 | 1186 ± 316* (83 ± 55) | 1198 ± 278* (95 ± 70) | 1199 ± 288** (95 ± 56) | 1276 ± 339* (172 ± 151) |
| | Astragaloside IV | 0.3 | 1055 ± 157 | 1082 ± 176 (27 ± 75) | 1141 ± 136* (86 ± 61) | 1167 ± 157*** (112 ± 31) | 1165 ± 112** (110 ± 67) |
| −dp/dt mmHg/s | Control | — | −859 ± 253 | −891 ± 325 (−31 ± 134) | −857 ± 345 (2 ± 124) | −824 ± 314 (36 ± 117) | −823 ± 227 (36 ± 85) |
| | CMG | 0.15 | −888 ± 310 | −865 ± 286 (22 ± 65) | −883 ± 288 (5 ± 36) | −875 ± 288 (13 ± 49) | −830 ± 277 (58 ± 77) |
| | CMG | 0.3 | −921 ± 311 | −958 ± 313 (−37 ± 44) | −925 ± 299 (−4 ± 80) | −947 ± 308 (−25 ± 74) | −937 ± 289 (−16 ± 91) |
| | CMG | 0.6 | −852 ± 244 | −850 ± 223 (2 ± 31) | −857 ± 238 (−4 ± 46) | −851 ± 196 (2 ± 98) | −842 ± 220 (10 ± 91) |
| | Astragaloside IV | 0.3 | −836 ± 194 | −878 ± 179 (−43 ± 104) | −882 ± 163 (−46 ± 118) | −847 ± 141 (−12 ± 124) | −875 ± 105 (−39 ± 142) |

TABLE 6-continued

The Effects of Intravenous Administration of CMG on Maximum Left Ventricular
Change Rate on Anesthetized Open-Chest Dogs ($\bar{x} \pm 8$, n = 6)

| Index | Groups | Dosage (mg/kg) | Before administration | After administration (min) | | | | |
|---|---|---|---|---|---|---|---|---|
| | | | | 30 | 45 | 60 | 90 | 120 |
| dp/dt mmHg/s | Control | — | 1288 ± 577 | 1319 ± 597 (31 ± 159) | 1313 ± 544 (25 ± 212) | 1337 ± 642 (49 ± 133) | 1309 ± 646 (21 ± 204) | 1296 ± 660 (8 ± 276) |
| | CMG | 0.15 | 1150 ± 391 | 1170 ± 425 (20 ± 157) | 1164 ± 356 (14 ± 86) | 1126 ± 375 (−24 ± 57) | 1121 ± 412 (−28 ± 90) | 1138 ± 387 (−11 ± 92) |
| | CMG | 0.3 | 1261 ± 453 | 1304 ± 459 (43 ± 100) | 1285 ± 453 (24 ± 83) | 1272 ± 479 (11 ± 94) | 1242 ± 437 (−19 ± 39) | 1309 ± 433 (48 ± 92) |
| | CMG | 0.6 | 1104 ± 295 | 1232 ± 274* (128 ± 108) | 1181 ± 320* (77 ± 53) | 1199 ± 294* (95 ± 76) | 1152 ± 313 (48 ± 63) | 1078 ± 283 (−25 ± 109) |
| | Astragaloside IV | 0.3 | 1055 ± 157 | 1140 ± 92 (85 ± 84) | 1124 ± 163 (69 ± 73) | 1098 ± 192 (43 ± 77) | 1100 ± 160 (45 ± 73) | 1088 ± 182 (33 ± 59) |
| −dp/dt mmHg/s | Control | — | −859 ± 253 | −900 ± 206 (−40 ± 119) | −884 ± 338 (−25 ± 175) | −842 ± 280 (17 ± 79) | −870 ± 401 (−11 ± 229) | −917 ± 423 (−58 ± 241) |
| | CMG | 0.15 | −888 ± 310 | −863 ± 258 (25 ± 79) | −854 ± 259 (34 ± 80) | −841 ± 249 (47 ± 92) | −857 ± 243 (31 ± 128) | −897 ± 263 (−9 ± 176) |
| | CMG | 0.3 | −921 ± 311 | −885 ± 293 (36 ± 97) | −878 ± 266 (43 ± 117) | −833 ± 236 (88 ± 199) | −909 ± 312 (12 ± 172) | −894 ± 278 (27 ± 63) |
| | CMG | 0.6 | −852 ± 244 | −833 ± 243 (20 ± 96) | −842 ± 170 (10 ± 126) | −829 ± 157 (24 ± 167) | −815 ± 238 (37 ± 55) | −789 ± 269 (64 ± 63) |
| | Astragaloside IV | 0.3 | −836 ± 194 | −807 ± 124 (28 ± 160) | −809 ± 137 (26 ± 159) | −788 ± 126 (48 ± 177) | −762 ± 139 (74 ± 184) | −748 ± 167 (88 ± 215) |

Note:
1. *p < 0.05, **p < 0.01 vs before administration in paired comparisons;
2. Numbers in brackets were the changes compared to before administration;
3. There was no significant difference between equal dosage of CMG and astragaloside IV.

TABLE 7

The Effects of Intravenous Administration of CMG on Cardiac Output and Total Peripheral
Resistance on Anesthetized Open-Chest Dogs ($\bar{x} \pm s$, n = 6)

| Index | Groups | Dosage (mg/kg) | Before administration | After Administration (min) | | | |
|---|---|---|---|---|---|---|---|
| | | | | 5 | 10 | 15 | 20 |
| CO L/min | Control | — | 1.15 ± 0.34 | 1.26 ± 0.42 (0.11 ± 0.11) | 1.20 ± 0.39 (0.05 ± 0.08) | 1.15 ± 0.39 (0.00 ± 0.08) | 1.26 ± 0.38 (0.11 ± 0.10) |
| | CMG | 0.15 | 1.21 ± 0.38 | 1.24 ± 0.38 (0.04 ± 0.09) | 1.31 ± 0.32 (0.10 ± 0.12) | 1.21 ± 0.26 (0.00 ± 0.15) | 1.19 ± 0.27 (−0.02 ± 0.15) |
| | CMG | 0.3 | 1.10 ± 0.38 | 1.16 ± 0.39 (0.06 ± 0.09) | 1.09 ± 0.39 (−0.01 ± 0.14) | 1.10 ± 0.38 (0.00 ± 0.17) | 1.08 ± 0.36 (−0.02 ± 0.06) |
| | CMG | 0.6 | 1.15 ± 0.40 | 1.18 ± 0.42 (0.03 ± 0.09) | 1.17 ± 0.33 (0.02 ± 0.11) | 1.20 ± 0.38 (0.05 ± 0.09) | 1.19 ± 0.34 (0.05 ± 0.10) |
| | Astragaloside IV | 0.3 | 1.20 ± 0.32 | 1.23 ± 0.36 (0.03 ± 0.05) | 1.24 ± 0.32 (0.04 ± 0.05) | 1.21 ± 0.30 (0.01 ± 0.04) | 1.20 ± 0.27 (0.00 ± 0.06) |
| CI L/min/m$^2$ | Control | — | 2.05 ± 0.78 | 2.24 ± 0.90 (0.19 ± 0.19) | 2.12 ± 0.84 (0.08 ± 0.15) | 2.04 ± 0.85 (0.00 ± 0.14) | 2.23 ± 0.83 (0.18 ± 0.17) |
| | CMG | 0.15 | 2.08 ± 0.63 | 2.15 ± 0.65 (0.07 ± 0.16) | 2.26 ± 0.55 (0.18 ± 0.20) | 2.09 ± 0.45 (0.01 ± 0.24) | 2.05 ± 0.45 (−0.03 ± 0.26) |
| | CMG | 0.3 | 1.98 ± 0.84 | 2.09 ± 0.86 (0.11 ± 0.16) | 1.96 ± 0.85 (−0.03 ± 0.23) | 1.98 ± 0.84 (−0.01 ± 0.28) | 1.94 ± 0.81 (−0.04 ± 0.11) |
| | CMG | 0.6 | 1.96 ± 0.54 | 2.00 ± 0.56 (0.04 ± 0.16) | 2.01 ± 0.39 (0.05 ± 0.20) | 2.05 ± 0.50 (0.09 ± 0.16) | 2.05 ± 0.41 (0.09 ± 0.18) |
| | Astragaloside IV | 0.3 | 2.14 ± 0.52 | 2.20 ± 0.59 (0.06 ± 0.10) | 2.21 ± 0.52 (0.07 ± 0.08) | 2.16 ± 0.51 (0.02 ± 0.07) | 2.15 ± 0.44 (0.00 ± 0.10) |
| TPR dyn·s/cm$^5$ | Control | — | 5133 ± 854 | 4854 ± 878 (−279 ± 283) | 4980 ± 903 (−153 ± 359) | 5203 ± 1036 (70 ± 557) | 4598 ± 682* (−535 ± 341) |
| | CMG | 0.15 | 5150 ± 2321 | 4967 ± 2135 (−183 ± 313) | 4568 ± 1871 (−582 ± 652) | 4612 ± 1333 (−538 ± 1075) | 4882 ± 1971 (−268 ± 672) |
| | CMG | 0.3 | 5299 ± 1597 | 5248 ± 1878 (−52 ± 829) | 5683 ± 2354 (384 ± 1293) | 5535 ± 2356 (236 ± 1386) | 5513 ± 1980 (214 ± 869) |
| | CMG | 0.6 | 5507 ± 2267 | 5474 ± 2219 (−32 ± 572) | 5261 ± 1874 (−246 ± 497) | 5249 ± 2234 (−258 ± 392) | 5176 ± 1818 (−331 ± 534) |
| | Astragaloside IV | 0.3 | 5224 ± 1465 | 5046 ± 1572 (−178 ± 384) | 5162 ± 1495 (−62 ± 517) | 5319 ± 1695 (95 ± 662) | 5203 ± 1464 (−21 ± 735) |

TABLE 7-continued

The Effects of Intravenous Administration of CMG on Cardiac Output and Total Peripheral Resistance on Anesthetized Open-Chest Dogs ($\bar{x} \pm s$, n = 6)

| Index | Groups | Dosage (mg/kg) | Before administration | After Administration (min) | | | | |
|---|---|---|---|---|---|---|---|---|
| | | | | 30 | 45 | 60 | 90 | 120 |
| CO L/min | Control | — | 1.15 ± 0.34 | 1.18 ± 0.38 (0.02 ± 0.05) | 1.20 ± 0.40 (0.05 ± 0.08) | 1.15 ± 0.48 (0.00 ± 0.18) | 1.13 ± 0.47 (−0.02 ± 0.16) | 1.17 ± 0.47 (0.01 ± 0.17) |
| | CMG | 0.15 | 1.21 ± 0.38 | 1.14 ± 0.24 (−0.07 ± 0.16) | 1.16 ± 0.22 (−0.04 ± 0.25) | 1.11 ± 0.21 (−0.10 ± 0.23) | 1.06 ± 0.20 (−0.15 ± 0.24) | 1.03 ± 0.19 (−0.17 ± 0.28) |
| | CMG | 0.3 | 1.10 ± 0.38 | 1.07 ± 0.36 (−0.03 ± 0.18) | 1.03 ± 0.39 (−0.07 ± 0.07) | 1.00 ± 0.45 (−0.10 ± 0.25) | 0.96 ± 0.47 (−0.14 ± 0.24) | 1.00 ± 0.52 (−0.10 ± 0.30) |
| | CMG | 0.6 | 1.15 ± 0.40 | 1.20 ± 0.43 (0.05 ± 0.07) | 1.15 ± 0.27 (0.00 ± 0.15) | 1.19 ± 0.32 (0.04 ± 0.13) | 1.22 ± 0.40 (0.07 ± 0.12) | 1.21 ± 0.38 (0.06 ± 0.13) |
| | Astragaloside IV | 0.3 | 1.20 ± 0.32 | 1.16 ± 0.29 (−0.04 ± 0.09) | 1.17 ± 0.32 (−0.03 ± 0.10) | 1.18 ± 0.34 (−0.02 ± 0.06) | 1.21 ± 0.32 (0.00 ± 0.05) | 1.20 ± 0.30 (0.00 ± 0.03) |
| CI L/min/m² | Control | — | 2.05 ± 0.78 | 2.09 ± 0.85 (0.05 ± 0.10) | 2.14 ± 0.91 (0.09 ± 0.15) | 2.06 ± 1.04 (0.02 ± 0.31) | 2.02 ± 1.00 (−0.03 ± 0.28) | 2.09 ± 1.01 (0.04 ± 0.30) |
| | CMG | 0.15 | 2.08 ± 0.63 | 1.98 ± 0.44 (−0.10 ± 0.27) | 2.02 ± 0.45 (−0.06 ± 0.43) | 1.92 ± 0.42 (−0.16 ± 0.39) | 1.83 ± 0.36 (−0.25 ± 0.39) | 1.79 ± 0.37 (−0.29 ± 0.45) |
| | CMG | 0.3 | 1.98 ± 0.84 | 1.92 ± 0.78 (−0.06 ± 0.30) | 1.85 ± 0.84 (−0.13 ± 0.13) | 1.80 ± 0.93 (−0.19 ± 0.42) | 1.74 ± 0.98 (−0.25 ± 0.42) | 1.81 ± 1.07 (−0.17 ± 0.52) |
| | CMG | 0.6 | 1.96 ± 0.54 | 2.05 ± 0.57 (0.09 ± 0.12) | 1.97 ± 0.30 (0.01 ± 0.26) | 2.04 ± 0.36 (0.08 ± 0.24) | 2.09 ± 0.53 (0.13 ± 0.20) | 2.07 ± 0.47 (0.11 ± 0.22) |
| | Astragaloside IV | 0.3 | 2.14 ± 0.52 | 2.08 ± 0.48 (−0.07 ± 0.17) | 2.08 ± 0.52 (−0.06 ± 0.19) | 2.10 ± 0.53 (−0.05 ± 0.11) | 2.15 ± 0.52 (0.01 ± 0.08) | 2.14 ± 0.50 (0.00 ± 0.06) |
| TPR dyn·s/cm⁵ | Control | — | 5133 ± 854 | 5050 ± 1087 (−83 ± 391) | 5062 ± 1209 (−71 ± 784) | 5360 ± 1469 (228 ± 960) | 5587 ± 1585 (455 ± 1014) | 5528 ± 1458 (396 ± 737) |
| | CMG | 0.15 | 5150 ± 2321 | 5045 ± 2043 (−105 ± 498) | 4951 ± 1731 (−199 ± 925) | 5112 ± 1599 (−38 ± 811) | 5576 ± 2153 (426 ± 770) | 5734 ± 1774 (584 ± 1030) |
| | CMG | 0.3 | 5299 ± 1597 | 5318 ± 2153 (19 ± 1444) | 6068 ± 2331 (768 ± 937) | 6625 ± 4423 (1326 ± 3485) | 7000 ± 4452 (1701 ± 3472) | 7219 ± 5040 (1920 ± 3990) |
| | CMG | 0.6 | 5507 ± 2267 | 5406 ± 2485 (−101 ± 366) | 5337 ± 1723 (−170 ± 595) | 5170 ± 1416 (−336 ± 1012) | 5285 ± 2431 (−222 ± 606) | 4925 ± 1674 (−582 ± 764) |
| | Astragaloside IV | 0.3 | 5224 ± 1465 | 5430 ± 1302 (206 ± 718) | 5301 ± 1638 (77 ± 552) | 5278 ± 1714 (54 ± 458) | 4952 ± 1517 (−272 ± 349) | 5046 ± 1440 (−178 ± 394) |

Note:
1. *p < 0.05, **p < 0.01 vs before administration in paired comparisons;
2. Numbers in brackets were the changes compared to before administration;
3. There was no significant difference between equal dosage of CMG and astragaloside IV.

TABLE 8

The Effects of Intravenous Administration of CMG on Coronary Circulation of Anesthetized Open-Chest Dogs ($\bar{x} \pm s$, n = 6)

| Index | Groups | Dosage (mg/kg) | Before administration | After administration (min) | | | |
|---|---|---|---|---|---|---|---|
| | | | | 5 | 10 | 15 | 20 |
| CF ml/min/100 g | Control | — | 54.0 ± 13.4 | 57.4 ± 13.8 (3.4 ± 4.0) | 58.3 ± 14.5 (4.3 ± 5.0) | 54.9 ± 13.4 (0.9 ± 6.7) | 56.4 ± 20.7 (2.4 ± 10.6) |
| | CMG | 0.15 | 57.7 ± 24.1 | 57 ± 21.7 (−0.7 ± 3.6) | 55.9 ± 21.6 (−1.8 ± 5.0) | 55.9 ± 22.2 (−1.8 ± 5.8) | 54.3 ± 20.4 (−3.4 ± 4.4) |
| | CMG | 0.3 | 50.2 ± 19.5 | 51.7 ± 20.7 (1.5 ± 5.3) | 53.5 ± 21.1 (3.3 ± 3.2) | 51.3 ± 21.1 (1.1 ± 4.2) | 51.4 ± 19.2 (1.2 ± 4.0) |
| | CMG | 0.6 | 51.2 ± 8.0 | 51.7 ± 10.5 (0.5 ± 3.1) | 51.2 ± 8.4 (0.0 ± 2.2) | 51.4 ± 8.3 (0.2 ± 3.7) | 49.8 ± 8.0 (−1.4 ± 1.4) |
| | Astragaloside IV | 0.3 | 57 ± 16.1 | 57.2 ± 14.0 (0.2 ± 3.5) | 59.0 ± 20.5 (2.0 ± 6.5) | 57.0 ± 22.3 (0.0 ± 7.2) | 59.1 ± 21.2 (2.1 ± 7.3) |
| CR mmHg/ml/min/100 g | Control | — | 1.37 ± 0.30 | 1.31 ± 0.35 (−0.05 ± 0.09) | 1.26 ± 0.30 (−0.1 ± 0.10) | 1.33 ± 0.31 (−0.03 ± 0.14) | 1.36 ± 0.53 (0.00 ± 0.26) |
| | CMG | 0.15 | 1.35 ± 0.44 | 1.35 ± 0.42 (−0.01 ± 0.08) | 1.36 ± 0.42 (0.00 ± 0.11) | 1.32 ± 0.38 (−0.03 ± 0.14) | 1.35 ± 0.39 (0.00 ± 0.13) |
| | CMG | 0.3 | 1.53 ± 0.67 | 1.57 ± 0.74 (0.04 ± 0.17) | 1.50 ± 0.71 (−0.03 ± 0.12) | 1.56 ± 0.76 (0.02 ± 0.15) | 1.51 ± 0.68 (−0.02 ± 0.14) |
| | CMG | 0.6 | 1.41 ± 0.35 | 1.44 ± 0.39 (0.02 ± 0.08) | 1.44 ± 0.40 (0.03 ± 0.12) | 1.43 ± 0.35 (0.01 ± 0.07) | 1.48 ± 0.36 (0.06 ± 0.10) |
| | Astragaloside IV | 0.3 | 1.40 ± 0.49 | 1.36 ± 0.47 (−0.05 ± 0.07) | 1.39 ± 0.45 (−0.01 ± 0.12) | 1.46 ± 0.50 (0.06 ± 0.15) | 1.37 ± 0.42 (−0.03 ± 0.16) |

TABLE 8-continued

The Effects of Intravenous Administration of CMG on Coronary Circulation of Anesthetized Open-Chest Dogs ($\bar{x} \pm s$, n = 6)

| Index | Groups | Dosage (mg/kg) | Before administration | After administration (min) | | | | |
|---|---|---|---|---|---|---|---|---|
| | | | | 30 | 45 | 60 | 90 | 120 |
| CF ml/min/ 100 g | Control | — | 54.0 ± 13.4 | 57.2 ± 16.0 (3.2 ± 6.8) | 59.0 ± 22.0 (5.1 ± 14.0) | 59.3 ± 20.7 (5.4 ± 12.5) | 61.2 ± 21.9 (7.2 ± 14.0) | 61.6 ± 21.2 (7.7 ± 14.2) |
| | CMG | 0.15 | 57.7 ± 24.1 | 52.5 ± 16.9 (−5.2 ± 7.9) | 51.6 ± 17.1 (−6.1 ± 8.1) | 51.8 ± 15.0 (−5.9 ± 9.9) | 53.7 ± 14.3 (−4.0 ± 10.4) | 56.5 ± 16.6 (−1.2 ± 13.7) |
| | CMG | 0.3 | 50.2 ± 19.5 | 51.4 ± 24.5 (1.2 ± 6.2) | 51.7 ± 23.5 (1.6 ± 6.8) | 51.7 ± 23.9 (1.6 ± 6.8) | 51.1 ± 19.1 (1.0 ± 4.7) | 50.7 ± 20.1 (0.5 ± 2.0) |
| | CMG | 0.6 | 51.2 ± 8.0 | 50.7 ± 8.5 (−0.5 ± 4.0) | 50.4 ± 7.8 (−0.8 ± 4.7) | 50.2 ± 11.6 (−1.0 ± 6.9) | 48.6 ± 7.2 (−2.6 ± 2.8) | 49.3 ± 7.3 (−1.9 ± 5.0) |
| | Astragaloside IV | 0.3 | 57 ± 16.1 | 57.8 ± 16.6 (0.8 ± 3.2) | 54.0 ± 15.0 (−2.9 ± 7.7) | 53.7 ± 18.1 (−3.3 ± 5.1) | 57.4 ± 19.0 (0.4 ± 9.5) | 55.6 ± 19.7 (−1.4 ± 11.1) |
| CR mmHg/ml/ min/100 g | Control | — | 1.37 ± 0.30 | 1.29 ± 0.31 (−0.08 ± 0.13) | 1.31 ± 0.42 (−0.05 ± 0.16) | 1.26 ± 0.36 (−0.11 ± 0.15) | 1.27 ± 0.50 (−0.09 ± 0.22) | 1.28 ± 0.41 (−0.09 ± 0.18) |
| | CMG | 0.15 | 1.35 ± 0.44 | 1.38 ± 0.38 (0.02 ± 0.13) | 1.42 ± 0.39 (0.07 ± 0.20) | 1.38 ± 0.36 (0.03 ± 0.16) | 1.36 ± 0.37 (0.00 ± 0.24) | 1.35 ± 0.44 (−0.01 ± 0.25) |
| | CMG | 0.3 | 1.53 ± 0.67 | 1.51 ± 0.74 (−0.02 ± 0.09) | 1.65 ± 0.92 (0.11 ± 0.29) | 1.54 ± 0.75 (0.01 ± 0.19) | 1.51 ± 0.66 (−0.02 ± 0.16) | 1.60 ± 0.82 (0.07 ± 0.21) |
| | CMG | 0.6 | 1.41 ± 0.35 | 1.46 ± 0.38 (0.04 ± 0.08) | 1.48 ± 0.35 (0.06 ± 0.16) | 1.53 ± 0.47 (0.11 ± 0.26) | 1.52 ± 0.37 (0.11 ± 0.12) | 1.42 ± 0.27 (0.00 ± 0.17) |
| | Astragaloside IV | 0.3 | 1.40 ± 0.49 | 1.41 ± 0.47 (0.00 ± 0.13) | 1.44 ± 0.50 (0.04 ± 0.25) | 1.51 ± 0.64 (0.10 ± 0.23) | 1.43 ± 0.83 (0.02 ± 0.51) | 1.51 ± 0.82 (0.11 ± 0.41) |

Note:
1. There was no significant difference compared to before administration;
2. Numbers in brackets were the changes compared to before administration;
3. There was no significant difference between equal dosage of CMG and astragaloside IV.

The invention claimed is:

1. A method for preparing cycloastragenol-6-O-β-D-glucoside, characterized by comprising the following steps:
   a. using astragaloside IV or Astragali extracts prepared by a conventional method as raw materials and adding an appropriate solvent thereinto to form a raw material solution; when the raw material is astragaloside IV, the concentration of astragaloside IV in the solution is 0.01-0.1% W/V; and when the raw material is Astragali extracts, the ratio of extracts:solution is 1:15-1:1000 W:V;
   b. adding hydrolase and allowing for hydrolysis at a constant temperature to obtain a hydrolysate, wherein said hydrolysis is conducted for 12-72 hours at a constant temperature from 40 to 55° C. and a suitable pH of the solution is from 4 to 7, said hydrolase being selected from the group consisting of β-glycosidase, β-glucosidase, and a mixture of one of these enzymes and one or more enzymes selected from the group consisting of cellulase, glucanase, xylanase, glucoamylase, pectinase and amylase; and when the substrate is astragaloside IV, the ratio of the substrate to the enzymes is 1:1-50 W:W; and when the substrate is Astragali extracts, the ratio of the enzymes to the substrate is 1:100-10:1 W:W;
   c. separating the hydrolysate with macroporous adsorption resin; wherein when the raw material is Astragali extracts, the ratio of raw material:resin is 1:20-4:1 g:ml; and when the raw material is astragaloside IV, the ratio of raw material:resin is 0.1:1-20:1 mg:ml, wherein said separation is conducted by a process comprising
   subjecting the hydrolyzate to a macroporous adsorption resin with styrene as the skeleton,
   firstly eluting with 1-2 column volumes of water, then eluting with 1-2 column volumes of 0.5-2% alkali solution, then
   eluting with 1-3 column volumes of 20-40% ethanol solution, and finally
   eluting with 1-3 column volumes of 70-95% ethanol, and
   collecting the portion of eluent eluted with ethanol at a high concentration, followed by vacuum concentration; and
   d. purifying the separated product.

2. The method according to claim 1, characterized in that said solvent is selected from the group consisting of water, low alcohol, and aqueous low alcohol.

3. The method according to claim 2, characterized in that the concentration of said alcohol in the raw material solution is 1-30% V/V.

4. The method according to claim 2, characterized in that the low alcohol is a monohydric alcohol having from 1 to 3 carbon atoms.

5. The method according to claim 2, characterized in that the low alcohol is selected from the group consisting of ethanol and methanol.

6. The method according to claim 2, characterized in that the low alcohol is ethanol.

7. The method according to claim 2, characterized in that the concentration of the low alcohol in the raw material solution is 5-20% V/V.

8. The method according to claim 1, characterized in that said purification is conducted via a process comprising the following steps of:
   filtering the separated product, re-dissolving it in a low alcohol or an aqueous low alcohol, filtering, concentrating the filtrate and placing it until crystals precipitate, filtering to obtain the crystals, and then recrystallizing it with a low alcohol or an aqueous low alcohol to obtain cycloastragenol-6-O-β-D-glucoside with a purity of more than 95%.

9. The method according to claim 8, characterized in that the low alcohol in the purification step is selected from the group consisting of monohydric alcohols having from 1 to 5 carbon atoms and polyhydric alcohols.

10. The method according to claim 8, characterized in that the low alcohol in the purification step is selected from the group consisting of methanol and ethanol.

11. The method according to claim 1, characterized in that the hydrolase is β-glycosidase, β-glucosidase or xylanase.

12. The method according to claim 1, characterized in that the hydrolase is xylanase.

13. The method according to claim 1, characterized in that when the substrate is Astragali extracts, the ratio of the enzymes to the substrate is 1:50-10:1 W:W in step b.

14. The method according to claim 1, characterized in that when the raw material is Astragali extracts, the ratio of raw material:resin is 1:10-3:1 g/ml in step c.

15. The method according to claim 1, characterized in that when the raw material is astragaloside IV, the ratio of raw material:resin is 2:1-10:1 mg/ml in step c.

16. The method according to claim 1, characterized in that the hydrolysis is conducted for 48-72 hours.

* * * * *